(12) United States Patent
Palaniappan

(10) Patent No.: US 8,389,012 B2
(45) Date of Patent: Mar. 5, 2013

(54) GELLAN-GUM NANOPARTICLES AND METHODS OF MAKING AND USING THE SAME

(75) Inventor: Ravi Palaniappan, Lawrenceville, GA (US)

(73) Assignee: The Corporation of Mercer University, Macon, GA (US)

( * ) Notice: Subject to any disclaimer, the term of this patent is extended or adjusted under 35 U.S.C. 154(b) by 631 days.

(21) Appl. No.: 12/400,295

(22) Filed: Mar. 9, 2009

(65) Prior Publication Data

US 2010/0112076 A1   May 6, 2010

Related U.S. Application Data

(60) Provisional application No. 61/068,503, filed on Mar. 7, 2008.

(51) Int. Cl.
*A61K 9/14* (2006.01)
(52) U.S. Cl. ......................................... 424/489
(58) Field of Classification Search .................. None
See application file for complete search history.

(56) References Cited

U.S. PATENT DOCUMENTS

| 4,822,534 | A | | 4/1989 | Lencki et al. |
| 5,342,626 | A | * | 8/1994 | Winston et al. ............ 424/461 |
| 5,516,543 | A | | 5/1996 | Amankonah |
| 6,172,219 | B1 | | 1/2001 | Callegaro et al. |
| 6,203,680 | B1 | * | 3/2001 | Cole ........................... 204/469 |
| 2003/0072805 | A1 | * | 4/2003 | Miyazawa et al. ............ 424/489 |
| 2005/0031691 | A1 | * | 2/2005 | McGurk et al. .............. 424/484 |

OTHER PUBLICATIONS

Panyam, Jayanth, et al., Rapid endo-lyosomal escape of poly(DL-lactide-co-glycolide) nanoparticles: implications for drug and gene delivery, FASEB Journal, vol. 16, Aug. 2002, pp. 1217-1226.
Webpage, Carbodiimide Coupling Using EDC, http://people.clarkson.edu/ekatz/edc.htm Feb. 2008.
Babu, R.J. et al., "Formulation of Controlled Release Gellan Gum Macro Beads of Amoxicillin," Current Drug Deliever, 2010, vol. 7, pp. 36-43.
Majeti N. V. Ravi Kumar, et al., "Pharmaceutical Polymeric Controlled Drug Delivery Systems", Advances in Polymer Science, vol. 160, pp. 45-117, 2002.
Kedzierewicz F. et al., Abstract—"Effect of the formulation on the in-vitro release of propranolol from gellan beads", Int J Pharm. 1;178(1), pp. 129-136, 1999.

* cited by examiner

*Primary Examiner* — Susan Tran
(74) *Attorney, Agent, or Firm* — Withers & Keys, LLC

(57) ABSTRACT

Compositions containing a reaction product of gellan gum and polyethylene glycol are disclosed. Methods of making controlled-release gellan gum nanoparticles and methods of using controlled-release gellan gum nanoparticles are also disclosed.

13 Claims, 24 Drawing Sheets

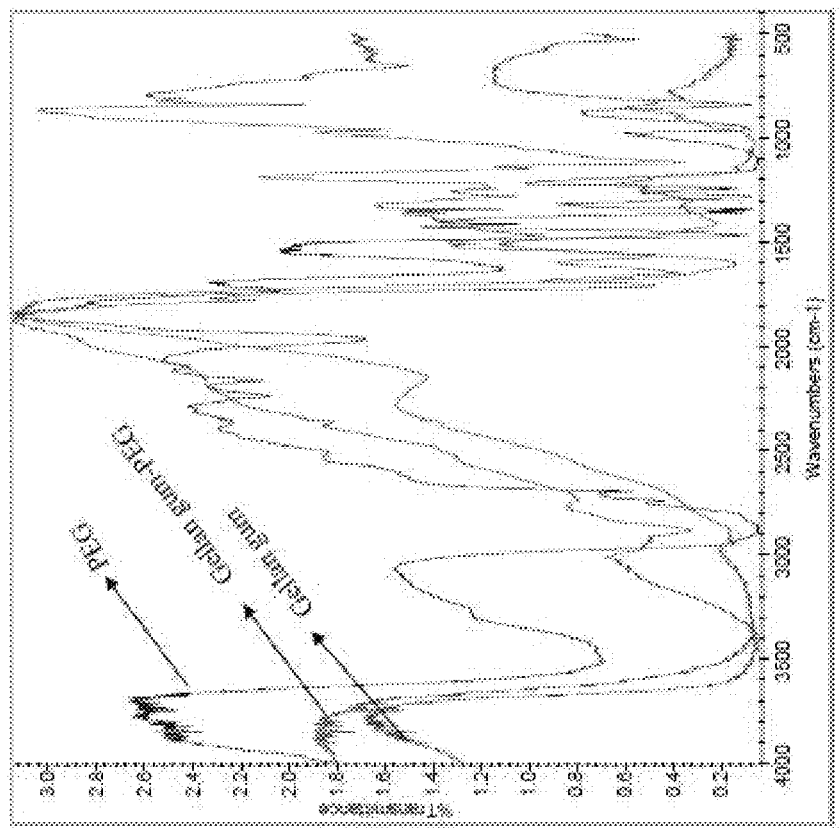
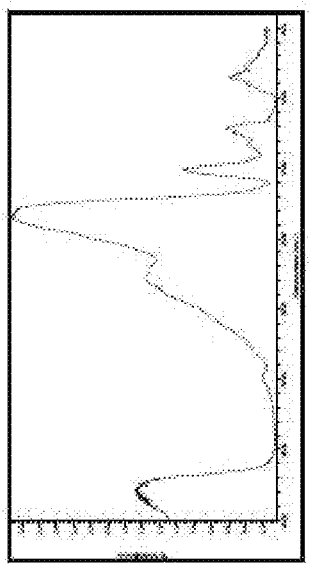
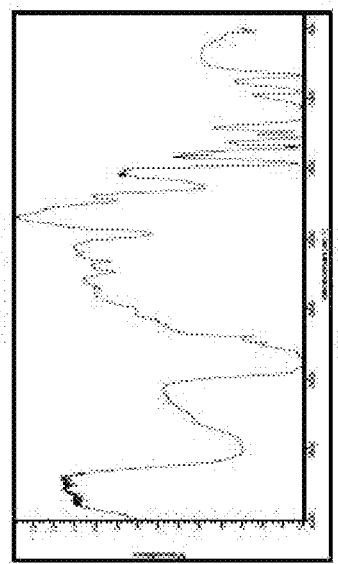
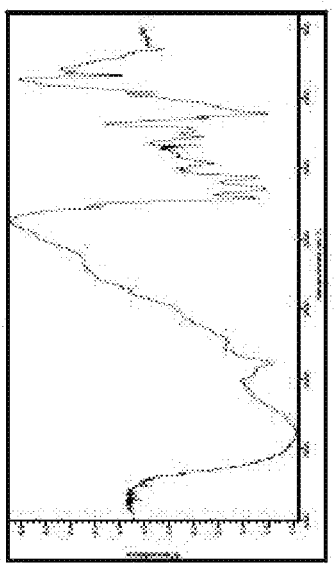
Figure 4A
Figure 4B
Figure 4C
Figure 4D

GELLAN-GUM NANOPARTICLES AND METHODS OF MAKING AND USING THE SAME

CROSS-REFERENCE TO RELATED APPLICATIONS

This patent application claims the benefit of priority to U.S. Provisional Patent Application Ser. No. 61/068,503 filed on Mar. 7, 2008 and entitled "GELLAN-GUM NANOPARTICLES AND METHODS OF MAKING AND USING THE SAME", the subject matter of which is hereby incorporated by reference in its entirety.

TECHNICAL FIELD

The present invention relates to compositions containing a reaction product of gellan gum and polyethylene glycol (PEG). The present invention also relates to methods of making controlled-release gellan gum nanoparticles and methods of using controlled-release gellan gum nanoparticles, for example, as a drug delivery device.

BACKGROUND

Gellan gum is an exocellular, microbial polysaccharide produced by Pseudomonas elodea and has been employed as a food additive. According to the FDA (21 CFR §172.665) gellan gum "may be safely used as a direct food additive for human consumption." The structural formula for gellan gum has been studied extensively and reported to consist of repeating tetrasaccharide units with the following structure:

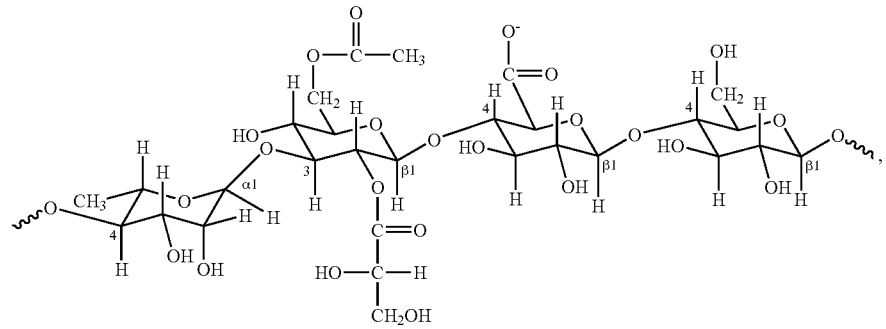

which can also be represented by:

-3-β-D-glcp-(1-4)-β-D-glcpA-1-4)-β-D-glcp-(1-4)-α-L-rhamp-(1- wherein "glcp" designates glucose, "glcpA" designates glucuronic acid, and "rhamp" designates rhamnose.

Gellan gum is commercially available in a clarified form under the trade designation KELCOGEL® for foods and industrial products and under the trade designation GELRITE® from CP Kelco, A Huber Company, (J.M. Huber Corporation, Edison, N.J.) for microbiological media, plant tissue culture, and pharmaceutical applications. Gellan gum has the potential to form gels in situ in the presence of mono- or divalent cations.

Gellan gum microparticles may be useful in encapsulating both bacteria and drugs (see, for example, U.S. Pat. Nos. 4,822,534 and 5,516,543). However, these gellan gum formulations of the prior art result in low biodistribution of encapsulated material, a feature attributed to susceptibility of the gellan gum polymer to degradation, which could present potential toxicity problems for applications such as anti-cancer drug delivery.

The physiological environment of tumors necessitates drug delivery systems that are capable of maintaining a controlled-release profile in acidic conditions. Thus, better formulations of gellan gum with improved controlled-release characteristics are needed for active drug targeting in vivo.

SUMMARY

The present invention addresses some of the difficulties and problems discussed above by the discovery of gellan gum compositions suitable for use as a drug delivery host, wherein the compositions comprise a reaction product of gellan gum and polyethylene glycol (PEG). The gellan gum compositions may be complexed with a biologically active substance to form a drug delivery complex comprising, for example, nanoparticles of the reaction product of gellan gum and PEG and a biologically active substance. In one exemplary embodiment, the biologically active substance comprises an anti-carcinogenic compound.

Accordingly, in one exemplary embodiment, the present invention is directed to a composition comprising a reaction product of gellan gum and PEG. In one exemplary embodiment of the present invention, gellan gum is reacted with a functionalized polyethylene glycol having one or more terminal end groups comprising (i) an amine group, (ii) a carboxyl group, or both (i) and (ii) to form gellan gum derivatives that are more biologically compatible, and are capable of maintaining a controlled-release profile in acidic environments. The present invention also comprises of gellan gum-PEG complex nanoparticles with functionalized surface, whereby the surface functionalization is accomplished via ligand or protein attachment either covalently or otherwise. In one exemplary embodiment, a bifunctional ligand (e.g., RNA-aptamer ligand) is covalently bonded to surfaces of gellan gum-PEG nanoparticles so as to provide an enhanced affinity for a particular material (e.g., a protein).

The present invention is further directed to a method of making a biocompatible, biodegradable and water-soluble gellan gum derivative, wherein the method comprises covalently bonding gellan gum to PEG. In some exemplary embodiments, the covalently bonding step comprises reacting a carboxylic acid group of the gellan gum with a carbodiimide to form an amine reactive intermediate; and reacting the amine reactive intermediate with a functionalized PEG having a terminal amine end group. In other embodiments, the amine reactive intermediate may be reacted with a functionalized PEG having a terminal amine end group and a carboxyl or hydroxyl terminal end group. In further embodiments, the carboxyl or hydroxyl terminal end group may be further reacted with a bifunctional ligand (e.g., RNA-aptamer ligand) so as to provide an enhanced affinity for a particular material (e.g., a protein) to the resulting gellan gum-PEG nanoparticles.

The present invention is even further directed to a method of delivering a drug to a patient, wherein the method comprises forming a drug delivery complex comprising (i) a reaction product of gellan gum and PEG alone or in combination with one or more additional bifunctional ligands (e.g., RNA-aptamer ligand), and (ii) a biologically active substance; and administering an effective amount of the drug delivery complex to the patient. In one exemplary embodiment, the reaction product of gellan gum and PEG comprises nanoparticles, and the biologically active substance comprises an anti-carcinogenic compound (e.g., paclitaxel).

These and other features and advantages of the present invention will become apparent after a review of the following detailed description of the disclosed embodiments and the appended claims.

BRIEF DESCRIPTION OF THE FIGURES

FIGS. 4A-D depict a comparison between the FTIR spectra of (a) gellan gum, (b) $NH_2$—PEG-COOH (c) exemplary gellan gum-b-PEG nanoparticles and (d) combined spectra of (a), (b) and (c);

DETAILED DESCRIPTION

Figure 1:
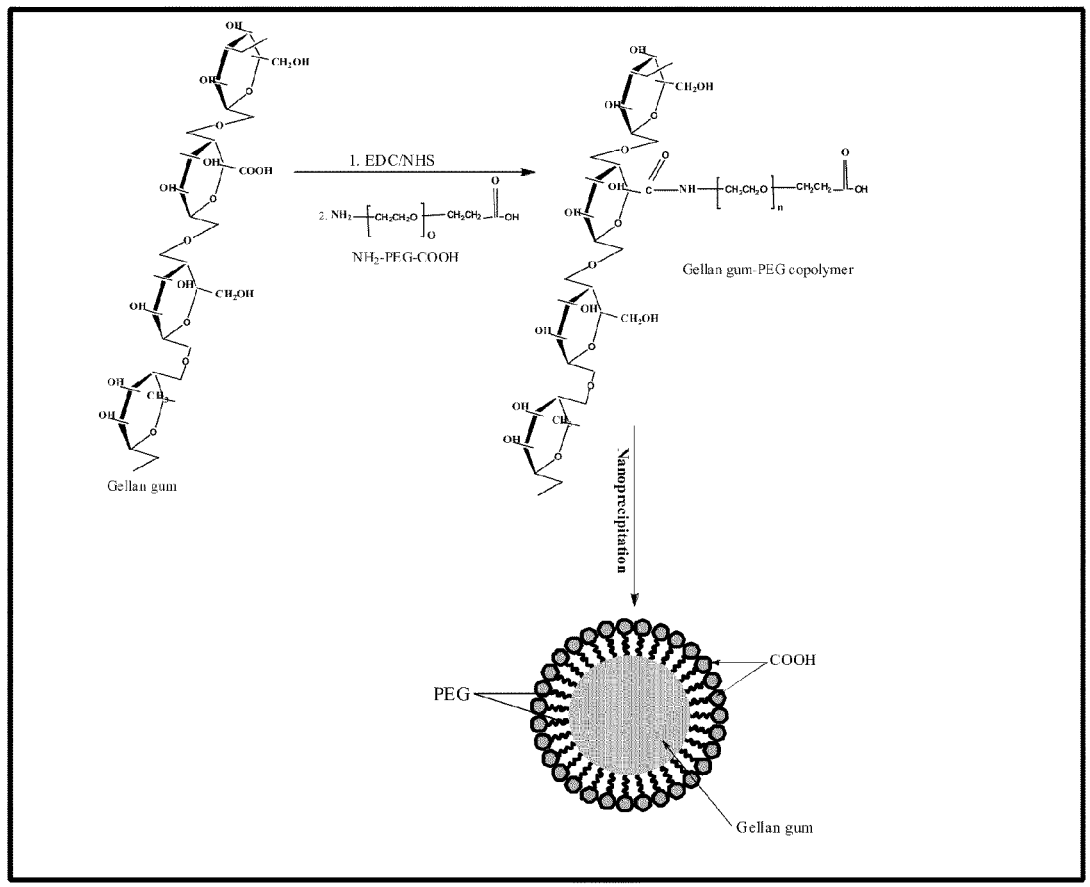
FIG. 1 depicts a view of a schematic representation of an exemplary method of forming gellan gum-b-PEG nanoparticles via a nanoprecipitation method.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to compositions containing a reaction product of gellan gum and PEG. The present invention is further directed to methods of making compositions containing a reaction product of gellan gum and PEG such as gellan gum nanoparticles. The present invention is even further directed to methods of using the reaction product of gellan gum and PEG in various applications including, for example, as a drug delivery device I. Reaction Product of Gellan Gum and PEG The present invention relates to conjugation of gellan gum to a hydrophilic component such as PEG or the likes. As used herein, gellan gum refers to the deacylated form of gellan gum or any of its salts, including, but not limited to, sodium gellan gum, potassium gellan gum, magnesium gellan gum, and calcium gellan gum. The gellan gum is covalently bonded to a hydrophilic component such as PEG or the likes to improve one or more properties of the gellan gum. PEG is a desired hydrophilic component due to the following properties: solubility in water, stability to heat, inertness to many chemical agents, non-immunogenicity, and nontoxicity. PEG is also considered to be bio-compatible, which is to say that it is capable of coexistence with living tissues or organisms without causing harm. When attached to a moiety having some desirable function in the body, the PEG tends to mask the moiety and can reduce or eliminate any immune response so that an organism can tolerate the presence of the moiety. Consequently, the present invention addresses previous problems such as toxicity and immunogenicity.

The present invention is directed to compositions containing a reaction product of gellan gum and PEG. In one exemplary embodiment, the PEG comprises a functionalized PEG. As used herein, the term "functionalized PEG" refers to one that has been chemically modified to have one or more terminal end groups. For example, functionalized PEG used in the present invention may have one or more terminal end groups comprising (i) an amine group, (ii) a carboxyl group, or both (i) and (ii). In one desired embodiment, the functionalized polyethylene glycol comprises amine polyethylene glycolic acid ($NH_2$—PEG-COOH).

Typically, the gellan gum covalently bonds to the functionalized PEG via a functional group along a glucuronic acid portion of the gellan gum. In some exemplary embodiments, the functional group along the glucuronic acid portion of the gellan gum is a carboxylic acid.

The gellan gum and PEG may be covalently linked to one another via any known linkage. Typically, the gellan gum and polyethylene glycol are covalently linked to one another via an amide linkage as described further below. For example, in some exemplary embodiments, the reaction product comprises gellan gum-b-PEG-COOH with an amide bond linkage between the gellan gum and polyethylene glycol.

In some desired embodiments, the reaction product comprises nanoparticles of gellan gum covalently bonded to polyethylene glycol. Typically, the nanoparticles have an average particle size ranging from about 50 nm to about 1000 nm depending on certain formulation parameters such as polymer ratios, stirring speed, stirring time and type of organic solvent used among others. Desirably, the nanoparticles have an average particle size ranging from about 50 nm to about 500 nm, even more desirably, from about 100 nm to about 350 nm.

Compositions comprising the reaction product of gellan gum and PEG may comprise the reaction product (e.g., in the form of nanoparticles) alone or in combination with additional composition components. In one exemplary embodiment, the compositions of the present invention further comprising a biologically active substance. Suitable biologically active substances include, but are not limited to, anti-carcinogenic compounds, proteins, small molecules etc.

To further improve the specificity of the disclosed nanoparticles, the nanoparticles may be further designed, for example, to target specific proteins expressed by target cells. One desired method of providing such specificity is to further functionalize the nanoparticle surfaces (e.g., the carboxyl groups of the GGbPEG nanoparticles) by covalently bonding thereto specific ligands (e.g. RNA aptamers) that are recognized by the expressed proteins. Such delivery design is capable of enhancing the in vivo targeting potentials and reducing toxicity, and thus increasing the bioavailability of encapsulated drugs.

In one desired exemplary embodiment, the functionalized nanoparticles comprise GGbPEG-Aptamer nanoparticles. These functionalized nanoparticles may be used to formulate a controlled-release formulation of Ptx-loaded-GGbPEG-Aptamer nanoparticles.

Other possible ligands that may be used to functionalize the GGbPEG nanoparticles of the present invention include, but are not limited to, RNA-aptamer ligand. Essentially any bifunctional ligand having (i) a first functional group capable of covalently bonding to a moiety on a GGbPEG nanoparticle and (ii) another moiety thereon that provides an affinity for a particular material (e.g., a protein) may be used in the present invention as a functionalizing ligand.

II. Method of Making a Reaction Product of Gellan Gum and PEG

The present invention further provides methods for making the reaction product of gellan gum and PEG. In one exemplary embodiment, the method comprises a method of making a biocompatible, biodegradable and water soluble gellan gum derivative comprising covalently bonding gellan gum to PEG. The method may comprise, for example, covalently bonding with an end-reactive PEG (e.g., a functionalized PEG) with a carboxyl acid group of gellan gum.

In one exemplary embodiment, the covalently bonding step comprises reacting a carboxylic acid group of the gellan gum with a carbodiimide to form an amine reactive intermediate, and reacting the amine reactive intermediate with a functionalized PEG substituted having a terminal amine end group. In other exemplary embodiments, the functionalized PEG further comprises a terminal carboxyl end group (e.g., amine polyethylene glycolic acid ($NH_2$—PEG-COOH)).

In some exemplary embodiments, the method includes dissolving the polyanionic polyssacharide (i.e., gellan gum) in cation-free distilled water at a temperature range of about 30° C. to about 120° C. and maintaining a pH environment of between about 4.5 to about 6.0 by addition of acid. Then, a carbodiimide and a nucleophile are added to the reaction mixture to activate a carboxyl moiety of the gellan polymer with the carbodiimide and the nucleophile and form an unstable amine-reactive intermediate. The unstable amine-reactive intermediate is subsequently reacted with a functionalized PEG such having at least one terminal amine end group to covalently bond the gellan gum via amide linkage.

In one desired embodiment, the above-described aqueous reaction mixture comprises a concentration of polyanionic polysaccharide of from about 0.2% to about 2.0% w/v, the acid comprises formic acid, the carbodiimide comprises 1-ethyl-3-(3-dimethylaminopropyl) carbodiimide, and the nucleophile comprises N-hydroxysuccinimide.

The method may further comprise forming nanoparticles from the gellan gum derivative (e.g., the reaction product of the gellan gum and the PEG). In one exemplary embodiment, the method of forming nanoparticles comprises dissolving the reaction product of the gellan gum and the PEG in a solvent (e.g., double deionized water) and precipitating the particles using a water miscible organic solvent such as isopropanol, tetrahydrofuran or acetone. Stirring may be carried out, for example, using a homogenizer (e.g., PowerGen 700D® homogenizer, Fisher Scientific (Pittsburgh, Pa.)) set at 10,000 rpm for 5 minutes at room temperature. The resulting nanoparticles may be recovered by ultracentrifugation, for example, at 30,000 rpm for 25 minutes and then dried under vacuum. One exemplary reaction scheme for forming nanoparticles from the reaction product of gellan gum and PEG is shown in FIG. 1.

As shown in the exemplary reaction scheme of FIG. 1, in a first step, gellan gum is reacted with amine polyethylene glycolic acid ($NH_2$—PEG-COOH) in the presence of 1-ethyl-3-(3-dimethylaminopropyl) carbodiimide (EDC) and N-hydroxysuccinimide (NHS) to form gellan gum-PEG-COOH. In a later step, the gellan gum-PEG-COOH is converted into nanoparticles.

The methods may further comprise forming specifically tailored, functionalized nanoparticles by covalently bonded one or more ligands onto the above-described nanoparticles. Any ligand may be used as long as the ligand covalently bonds thru the carboxyl groups of the above-described nanoparticles. In one exemplary embodiment, the method further comprises a step of covalently bonding RNA aptamer ligand to the above-described nanoparticles via the carboxyl groups of the gellan gum-PEG-COOH nanoparticles.

The methods may even further comprise forming a drug delivery complex comprising the above-described nanoparticles and a biologically active substance. In one exemplary embodiment, the biologically active substance comprises an anti-carcinogenic compound. The step of forming a drug delivery complex may simply comprise associating the above-described nanoparticles with a biologically active substance. In other embodiments, the step of forming a drug delivery complex may comprise encapsulating the biologically active substance within the above-described nanoparticles via a nanoprecipitation step (see, for example, FIG. 1). Encapsulation of biologically active substance within the above-described nanoparticles may also be achieved via other methods such as solvent evaporation and emulsion techniques among others.

III. Methods of Using the Reaction Product of Gellan Gum and Peg and Optional Ligand(s)

The present invention is even further directed to methods of using the reaction product of gellan gum and PEG in various applications. In one exemplary embodiment, the method of using the reaction product of gellan gum and PEG comprises a method of delivering a drug to a patient comprising forming a drug delivery complex comprising (i) a reaction product of gellan gum and PEG, and (ii) a biologically active substance, and administering an effective amount of the drug delivery complex to the patient. The method may comprise administering an effective amount of the drug delivery complex, wherein the reaction product comprises nanoparticles, and the biologically active substance comprises an anti-carcinogenic compound. In one desired embodiment, the nanoparticles comprise gellan gum-b-PEG with an amide bond linkage between the gellan gum and PEG.

In another exemplary embodiment, the method comprises using the reaction product of gellan gum, PEG and at least one ligand (e.g., RNA aptamer ligand) in a method of delivering a drug to a patient. The method may comprise forming a drug delivery complex comprising (i) a reaction product of gellan gum, PEG and at least one ligand (e.g., RNA aptamer ligand), and (ii) a biologically active substance, and administering an effective amount of the drug delivery complex to the patient. The method may comprise administering an effective amount of the drug delivery complex, wherein the reaction product comprises functionalized nanoparticles, and the biologically active substance comprises an anti-carcinogenic compound (e.g., paclitaxel (Ptx)). In one desired embodiment, the nanoparticles comprise gellan gum-b-PEG-RNA aptamer with an amide bond linkage between the gellan gum and PEG.

The reaction products (e.g., nanoparticles) of the present invention retain sufficient strength when hydrated to be useful as a drug delivery device. The nanoparticles show non-toxicity to normal human T-cells, and exhibit uptake and internalization in target cells such as human prostate cancer cells (PC-3).

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Materials

Paclitaxel, GELCORITE® (MW 1,000,000), 1-ethyl-3-(3-dimethylaminopropyl) carbodiimide hydrochloride ("EDC") (MW 191.7), N-hydroxysuccinimide ("NHS") (MW 115.5), tetrahydrofluran, acetone, isopropanol, albumin fluorescein isothiocyanate conjugate bovine (BSA-FITC), FITC dye, and tetrazolium dye 3-(4,5-dimethylthiazl-2-yl)-2,5-diphenyltetrazolium bromide (MTT) were purchased from Sigma Aldrich Chemical Company (St. Louis, Mo.). $NH_2$—PEG-COOH (MW 3400) was purchased from Necktar Therapeutics (San Carlos, Calif.) or Laysan Bio, Inc. (Arab, Ala., USA). Topro 3-iodide was purchased from Molecular Probes (Faraday Avenue, Calif., USA). IR-Dye 800 CW was purchased from Li-Cor Biosciences, NE USA. RNA-aptamer (sequence: 5'—$NH_2$-spacer-GGG/AGG/ACG/AUG/CGG/AUC/AGC/CAU/GUU/UAC/GUC/ACU/CCU/UGU/CAA/UCC/UCA/UCG/GCiT-3 with 2'-fluoro pyrimidines, a 5'-amino group attached by a hexaethyleneglycol spacer and a 3'-inverted T-cap was custom synthesized by RNA-TEC (Leuven, Belgium). In addition, RPMI 1640, fetal bovine serum ("FBS"), and penicillin/streptomycin ("P/S") were purchased from Sigma Aldrich Chemical Company (St. Louis, Mo.). Human T-cells were isolated from blood obtained from volunteer donors. Human prostate adenocarcinoma cell lines (PC-3 and DU-145) were purchased from ATCC (Manassas, Va., USA). Cells were maintained in RPMI-1640 supplemented with 10% FBS and 1% Penicillin-Streptomycin (100 U/ml penicillin; 100 μg/ml streptomycin). All reagents were analytical grade and used as received, unless otherwise stated. Stock solutions (1.0 M) of the methyl jasmonate (MJ) were prepared by dissolving in dimethyl sulfoxide (DMSO) and the aliquots stored at −20° C. prior to use.

Test Methods:

The following test methods were used to evaluate gellan gum-b-PEG-nanoparticles of the present invention:

Surface Morphology, Size and Charge of Nanoparticles

Morphological analysis of gellan gum-b-PEG nanoparticles was performed using transmission electron microscopy. Samples of nanoparticle suspensions (0.5 mg/ml) were dropped onto copper grids. After drying, particles were visualized using a Philips 201 (Philips/FEI, Briarcliff, Manor, N.Y.) transmission electron microscope following negative staining with 2% w/v uranyl acetate. In addition, the effect of gellan gum to PEG mass ratio on the final particle size was evaluated using Malvern Zetasizer, ZEN 1600 (Malvern Instruments, U.K). Dilute suspension of nanoparticles (50 μg/ml) was prepared using deionized water and particle size was measured with Malvern Zetasizer, ZEN1600. For the zeta potential measurement, nanoparticles were suspended in 1 mM KCl solution. The suspension was loaded into an optical well and zeta potential was measured using Malvern Zetasizer, ZEN1600.

Nuclear Magnetic Resonance (NMR) Spectroscopy $^1H$ (400 MHz) NMR spectra of (a) gellan gum, (b) $NH_2$—PEG-COOH, and (c) gellan gum-b-PEG-COOH nanoparticles were measured using nuclear magnetic resonance. 1.5 wt. percent gellan gum-b-PEG-COOH nanoparticle solutions in $D_2O$ were used for $^1H$ one-dimensional NMR experiments. Previous reports had shown that $^1H$ spectra with an acceptable signal to noise ratio for the determination of acetate and glycerate levels in gellan gum were obtainable in about 100 scans. Thus, an average of 120 scans was performed for each analysis.

Fourier Transform Infrared Spectroscopy (FTIR)

Possible chemical interaction between the nanoparticulate components was assessed using FTIR. Spectra were obtained using Nicolet Impact 410 (Nicolet Analytical Instrument (Madison, Wis.)) to assess the presence of amide linkages in the gellan gum-b-PEG nanoparticles. Spectra were obtained by a potassium bromide disc method. At each point, 128 spectra in the region of 500 to 4000 $cm^{-1}$ were averaged with a resolution of 2 $cm^{-1}$.

Determination of Unbound $NH_2$—PEG-COOH

The quantity of remaining unbound $NH_2$—PEG-COOH in a given gellan gum-b-PEG copolymer was determined by a method utilizing 2,4,6-trinitrobenzenesulfonic acid (TNBS; Sigma (St. Louis, Mo.)) as described by Pantam et al., *The FASEB Journal* 2002, Vol. 16, pp. 1217-26, the subject matter of which is hereby incorporated herein in its entirety. TNBS is known to react with amine groups of $NH_2$—PEG-COOH via a nucleophilic aromatic substitution, developing an orange dye.

Gellan gum-b-PEG-COOH copolymer (10.0 mg) was hydrated in a 0.10 M sodium tetraborate solution (Sigma (St. Louis, Mo.)) having a pH of about 9.3. Then, 0.15 mL of this solution was transferred to a 96-well microtitration plate and mixed with an equal volume of 0.03 M TNBS at room temperature (25±1° C.). The reaction was allowed to proceed for 45 minutes and the absorbance was measured at 420 nm (Precision Microplate Reader, Molecular Devices (Sunnyvale, Calif.)). The reagent blank consisted of 10 µl of 0.03 M TNBS in 0.15 mL of 0.10 M sodium tetraborate. The amount of free amino groups in gellan gum-b-PEG-COOH copolymer was calculated using a standard curve of $NH_2$—PEG-COOH (Necktar Therapeutics (San Carlos, Calif.) over the range from 2.0 to 80.0 mg/mL.

Rheological Studies

The effect of formulation parameters on the viscoelastic properties/mechanical strength of gellan gum-b-PEG nanoparticles was also studied using a cone and plate viscometer. Three different samples (F1-F3) and a control (i.e., unconjugated gellan gum) were hydrated in double deionized water to a final concentration of 1.5% (m/m). At one hour intervals, phase shift angle ($\delta$), shear stress ($\tau$) and shear deformation ($\gamma$) were determined. The storage modulus (G') and loss modulus (G") were automatically calculated using the formula:

$$G'=(\tau/\gamma)\cdot\cos\delta \quad G''=(\tau/\gamma)\cdot\sin\delta.$$

Furthermore, loss tangent (tan $\delta$), a parameter that represents the ratio between the loss modulus (G") and storage modulus (G') was determined. It has been reported that tan $\delta$ less than 1 signifies a formulation that behaves like gel, thus retains its hydrogel properties; however, if tan $\delta$ is greater than 1, the formulation has lost its gel characteristics and behaves more like fluid See, for example, Pantam et al., *The FASEB Journal,* 2002, Vol. 16, pp. 1217-26.

Determination of Thermal Stability by Differential Scanning Calorimetry (DSC)

The effect of gellan gum to PEG mass ratio on the thermal stability of gellan gum-b-PEG nanoparticle formulations was investigated using DSC. Samples (8.0 mg) from various formulations (F1-F5) comprising differing polymer ratios were characterized using this method. The experiment was performed by scanning these samples in sealed aluminum pans (Perkin-Elmer Inc., CT, USA) over the temperature range between 0 and 300° C. at a scanning rate of 5° C./min. An empty sealed aluminum pan was used as a reference. Nitrogen was used for purging the sample holders at a flow rate of 20 ml/min. The data presented represent an average of three separate experiments.

Toxicity Study Using Activated Human T-Cells

The effect of gellan gum-b-PEG nanoparticles on normal human T-cells was evaluated by method of dye exclusion assay. Primary human T cells from healthy blood donors were cultured in RPMI-1640 supplemented with 10% FBS and 1% Penicillin-Streptomycin (100 U/ml penicillin; 100 µg/ml streptomycin). Primary T cells were purified by Ficoll-Hypaque density gradient centrifugation. Following overnight incubation at 37° C. in $CO_2$ atmosphere, cells ($1\times10^6$) were incubated for 48 h in the presence of phytohemagglutinin (PHA) at a concentration of 5 µg/ml. Cells were then exposed to the growth medium containing varying concentrations (0.1-100 mg/ml) of gellan gum-b-PEG nanoparticles and further incubated for 24 h, 42 h and 72 h. At the end of the incubation period, cells were harvested and counted using hemacytometer. The effect of nanoparticles on normal human T-cells was accessed by direct evaluation of cell viability. Cytotoxicity was calculated relative to the untreated control as shown below:

$$\text{Percent viability} = \frac{\text{Number of live cells in the treatment group} \times 100}{\text{Number of live cells in the untreated control}}$$

$$\text{Percent cytotoxicity} = 100 - \text{calculated percent viability.}$$

Analysis of Gellan Gum-b-PEG Nanoparticle Uptake and Localization via Microscopy Human prostate adenocarcinoma cell line (PC-3) at $1\times10^5$ cells/100 mm plate was seeded and incubated overnight to allow for cell adhesion. To study the internalization and localization of gellan gum-b-PEG nanoparticles, cells in normal growth medium (RPMI 1640 supplemented with 10% FBS and 1% Penicillium/streptomycin) were replaced with a suspension of fluorescent nanoparticles (30 µg/ml) containing BSA-FITC and then incubated for 2 h followed by washing 2× with PBS. Cells were further incubated with TOPRO-3 iodide (100 nM; Molecular Probes) to conterstain nuclei and then mounted onto slides using mounting medium (DAKO). Images were captured by use of a 488-nm filter (fluorescein), 568-nm filter (rhodamine). Differential interference contrast using a Zeiss Confocal microscope LSM410 equipped with argon-krypton laser (Carl Zeiss Microimaging, Thornwood, N.Y.) were overlaid to obtain images to determine localization of nanoparticles inside the cell compartments.

In Vivo Biodistribution of GGbPEG-Apt Copolymeric Nanoparticles

GGbPEG-Apt bioconjugation was confirmed by evaluating the in vivo targeting potentials of fluorescent-loaded GGbPEG-Apt nanoparticles in athymic nude mice bearing human xenograft prostate tumor. All animal studies were carried out under the Mercer University IAUCUC approved protocol and in compliance with NIH's Principles of Laboratory Animal Care.

Human xenograft prostate cancer tumors were induced in 6-week old athymic nude mice (NCI Frederick, Md., USA). Mice were injected subcutaneously in the right flank with $2.5\times10^6$ PC-3 cells suspended in a 1:1 mixture of serum-free media and matrigel (BD Biosciences, Franklin Lakes, N.J., USA). Prior to use in tumor induction, PC-3 cells were cultured in RPMI-1640 medium supplemented with 10% fetal bovine serum, 100 units/ml penicillin G, and 100 mg/ml streptomycin. Tumor targeting studies were carried out after the mice developed ~150 mm³ tumors. Mice were divided into four groups, minimizing tumor size variations between groups. Mice were anesthetized by intraperitoneal injection of avertin (200 mg/kg body weight), and dosed with saline, IR-Dye 800 CW (Li-cor Biosciences, NE, USA), IR-Dye 800 CW-loaded GGbPEG nanoparticles, IR-Dye 800 CW-loaded GGbPEG-Apt nanoparticles via tail vein injection. The biodistribution of injected nanoparticles were traced using Odyssey infra-red imaging system (Li-cor Biosciences, NE, USA) for various time points up to three weeks.

Determination of Drug Content in GGbPEG Nanoparticles

The Ptx content in the GGbPEG copolymeric nanoparticles was determined by HPLC. An isocratic reverse-phase HPLC was performed on an Agilent 1100 series HPLC system (Agilent Technologies, Wilmington, Del.) using a Symmetry column (Waters, Milford, Mass.). The mobile phase consisted of acetonitrile-water (45:55 v/v) with a flow rate of 1.0 ml/min. The column effluent was detected at 227 nm with a variable wavelength detector (G1314A, JP11615541, UV detector, USA). The column temperature was maintained at 35° C. and the injected volume of the sample was 20 µl. The drug concentrations in the samples were obtained using a calibration curve.

Ptx content was investigated in an aqueous medium containing a hydrotropic agent: sodium salicylate. The freeze-dried drug containing polymeric nanoparticles were weighed, and then dissolved in deionized water containing 1 M sodium salicylate and vortexed for 15 minutes. Ptx was obtained from the supernatant after centrifugation at 20,000 rpm for 15 minutes and the content was measured by HPLC. Drug loading efficiency (L.E.) (%) and drug encapsulation efficiency (E.E.) (%) were calculated as follow:

$$L.E. \ (\% \ w/w) = \frac{\text{Mass of drug in nanoparticles} \times 100}{\text{Mass of nanoparticles}}$$

$$E.E. \ (\%, \ w/w) = \frac{\text{Mass of drug in nanoparticles} \times 100}{\text{Mass of feed drug}}$$

Surface Morphology and Particle Size of Drug-Loaded Nanoparticles

Particle size was determined using dynamic light scattering technique. Diluted suspension of nanoparticles (50 µg/ml) was prepared using deionized water and particle size was measured with Malvern Zetasizer, ZEN1600 (Malvern Instruments, UK). The analysis was performed at a scattering angle of 90° at room temperature. Data reported represent the mean±standard deviation of at least three different batches of nanoparticles. Furthermore, morphological analysis of nanoparticles was performed by transmission electron microscopy following negative staining with 2% w/v uranyl acetate.

Surface Charge

The surface stability of nanoparticles was also evaluated using zeta ($\zeta$) potential as the measuring parameter. The zeta potential measurement was obtained using the Malvern Zetasizer, ZEN1600 (Malvern Instruments, UK). Particles were suspended in 1 mM KCl solution; the suspension was loaded into an optical well and zeta potential measurements were obtained. Values reported are the mean±standard deviation of at least three different batches of nanoparticles.

X-ray Diffraction Studies

To study the molecular arrangement of Ptx in the GGbPEG copolymeric nanoparticles, powder X-ray diffraction patterns were acquired at room temperature on a Philips PW 1729 diffractometer (Eindhoven, Netherlands) using Cu Kα radiation. The data were collected over an angular range from 5° to 50° 2θ in continuous mode using a step size of 0.02° 2θ and step time of 5 seconds.

In vitro Release Study of Ptx-GGbPEG Nanoparticles

In vitro release profile of Ptx from the polymeric nanoparticles was investigated in an aqueous medium containing sodium salicylate. The freeze-dried drug containing polymeric nanoparticles were weighed, dissolved in 1 ml of deionized water, and introduced into a dialysis membrane bag (MWCO=6000-8000 Da). The release experiment was initiated by placing the endsealed dialysis bag in 20 ml of 1 M sodium salicylate solution at 37° C. The release medium was stirred at a speed of 100 rpm and at predetermined time intervals, samples (2 ml) were withdrawn and replaced with an equal volume of fresh medium (1 M sodium salicylate). The concentration of Ptx in samples was measured by HPLC as described earlier.

In Vitro Anti-Cancer Activity on Advanced Human Prostate Carcinoma Cells

To investigate the cytotoxicity of Ptx-GGbPEG-Apt nanoparticles on human prostate cancer cells, mitochondrial dehydrogenase assay (MTT) was employed. PC-3 or DU-145 cells ($5 \times 10^3$) were seeded in 96-well plates containing 100 µl of RPMI medium 1640 (American Type Culture Collection), supplemented with 100 units/ml aqueous penicillin G, 100 µg/ml streptomycin, and 10% FBS. Cells were then allowed to adhere overnight prior to treatment. On the day of experiment, cells were washed twice with PBS and then exposed to similar concentrations (25 µg/ml) of Ptx in either the encapsulated or free formulations. The control cells received 1% (v/v) DMSO or drug free GGbPEG nanoparticles (1.0 µg/ml). Cells were incubated with drug formulations for different time points (10, 30, 120 mins) followed by washing with PBS and replacing treatment medium with fresh medium in the plates. Cells were further incubated for 72 h. At the end of treatment period, medium was removed and replaced with 100 µl of complete culture medium and 10 µl of MTT (5 mg/ml) in each well and the plates were incubated at 37° C. in a humidified, 5% $CO_2$ atmosphere for 3 h. The resulting formazan crystals were solubilized with 100 µl of the stop solution (0.1N HCl in isopropanol). The optical densities (OD) of the resulting solutions were determined at 490 nm using a microplate reader (Packard Instruments, Meriden, Conn.) and cell viability (%) was calculated by comparing the OD of the treatment group relative to that of the untreated control group (100%).

$$\text{Cell Viability (\%)} = \frac{OD \text{ of treatment} - \text{Blank } OD \times 100}{OD \text{ of control} - \text{Blank } OD}$$

Colony Formation Assay (CFA)

The long-term effect of Ptx-GGbPEG-Apt nanoparticles on DU-145 and PC-3 cells was studied using CFA. Cells ($10^4$/plate) were seeded in 60 mm tissue culture plates and incubated overnight to allow for cell attachment. Then, cells were exposed to 25 µg/ml of Ptx-GGbPEG-Apt nanoparticles and incubated for 24 h or 48 h. The control groups received either 0.1% v/v DMSO or nanoparticles alone. At the end of incubation, cells from each treatment group were trypsinized, counted and plated into new 60 mm tissue culture plates (500 cells/plate) sufficient to yield a minimum of 100 colonies in the untreated control groups. Cells were then incubated in complete culture medium for up to 14 days undisturbed. On day 14, colonies were washed gently with 1×PBS, stained with crystal violet (0.5 g/100 ml in 95% ethanol) and surviving colonies were counted. Colonies containing at least 50 cells were scored and considered to have survived the treatment. The surviving fraction at each dose was calculated relative to the colony number in the untreated control groups. Data obtained represent at least two separate experiments.

$$\text{Surviving fraction} = \frac{\text{Plating efficiency of the treated group}}{\text{Plating efficiency of the untreated control}}$$

In Vivo Studies Using Athymic Nude Mice Bearing Human Xenograft Prostate Cancer Tumor For in vivo efficacy study, athymic nude mice bearing human prostate tumor (~150 mm$^3$) were divided into five groups of four mice, minimizing, weight and tumor size differences. All animal studies were carried out under the Mercer University IAUCUC approved protocol and in compliance with NIH's Principles of Laboratory Animal Care. Human xenograft prostate cancer tumors were induced in 6-week old athymic nude mice (NCI Frederick, Md., USA). Mice were injected subcutaneously in the right flank with $2.5 \times 10^6$ PC-3 cells suspended in a 1:1 mixture of serum-free media and matrigel (BD Biosciences, Franklin Lakes, N.J., USA). Prior to use in tumor induction, PC-3 cells were cultured in RPMI-1640 medium supplemented with 10% fetal bovine serum, 100 units/ml penicillin G, and 100 mg/ml streptomycin. Tumor targeting studies were carried out after the mice developed ~150 $mm^3$ tumors. Using maximal tolerated dose (MTD) of 40 mg/kg i.v Ptx as a reference point, tumor-bearing nude mice were treated by intravenous injection of saline, GGbPEG nanoparticles without drug, Ptx (40 mg/kg), Ptx-GGbPEG (40 mg/kg), or Ptx-GGbPEG-Apt (40 mg/kg). After dosing, the mice were monitored for weight and implanted tumor size daily for sixty days. The length and width of the tumors were measured by digital calipers and tumor volume was calculated by the following formula: $(width^2 \times length)/2$ [17]. The initial volume of the tumors averaged 155 $mm^3$ and the average body weight for mice in the study was 22.6 g.

Histological Analysis of Tumor

Selected tumors from each group were harvested and fixed in 10% neutral buffered formalin. Tumors were paraffin embedded, sectioned, placed on polylysine slides, and stained with Hematoxylin & Eosin (H & E) to visualize morphological changes in the tumors in both the treated and control groups. Images were recorded using a light microscope equipped with camera.

Statistical Analysis

Results were expressed as mean±SD of replicate analyses. Data analyses were performed (where appropriate) using ANOVA for a single factor, factorial treatment model with one way blocking to examine the effects of two factors and the differences at the many levels within each factor. Differences with p-values less than 0.05 ($p<0.05$) were considered as statistically significant.

Example 1

Synthesis of Gellan Gum-b-PEG

Gellan gum-b-PEG block copolymer with terminal carboxylate end groups was synthesized via a carbodiimide activation method by covalently bonding COOH-PEG-$NH_2$ onto carboxylic acid moieties present on the glucuronic portions of a gellan gum polymer as described below.

Gellan gum (250 mg, 0.00025 mmol) in demineralized water (10 ml) was converted to gellan-gum-NHS with excess N-hydroxysuccinimide (NHS) (50 mg, 0.43 mmol) in the presence of 1-ethyl-3-(3-dimethylaminopropyl)-carbodiimide (EDC) (80 mg, 0.42 mmol). The reaction was allowed to proceed for 1 h at room temperature. Then, COOH-PEG-$NH_2$ (50 mg, 0.015 mmol) was added to the reaction vessel, and the reaction was monitored for 12 h with stirring at room temperature. The reaction was performed at a pH range of from about 4.5 to about 5.5 using formic acid to prevent complete protonation of the free amine groups in the COOH-PEG-$NH_2$ reactant.

Gellan gum-b-PEG-COOH block copolymer was precipitated using tetrahydrofuran and washed with the same solvent (2×7 ml) to remove unreacted PEG and residual NHS. The resulting gellan-gum-PEG-COOH block co-polymer was dried under vacuum and used in nanoparticle preparations without further treatments as described below.

Example 2

Formulation of Gellan Gum-b-PEG-COOH Nanoparticles

A nanoprecipitation method was employed to form gellan gum-b-PEG nanoparticles (also referred to herein as "GGb-PEG copolymeric nanoparticles") as described below.

Figure 2:
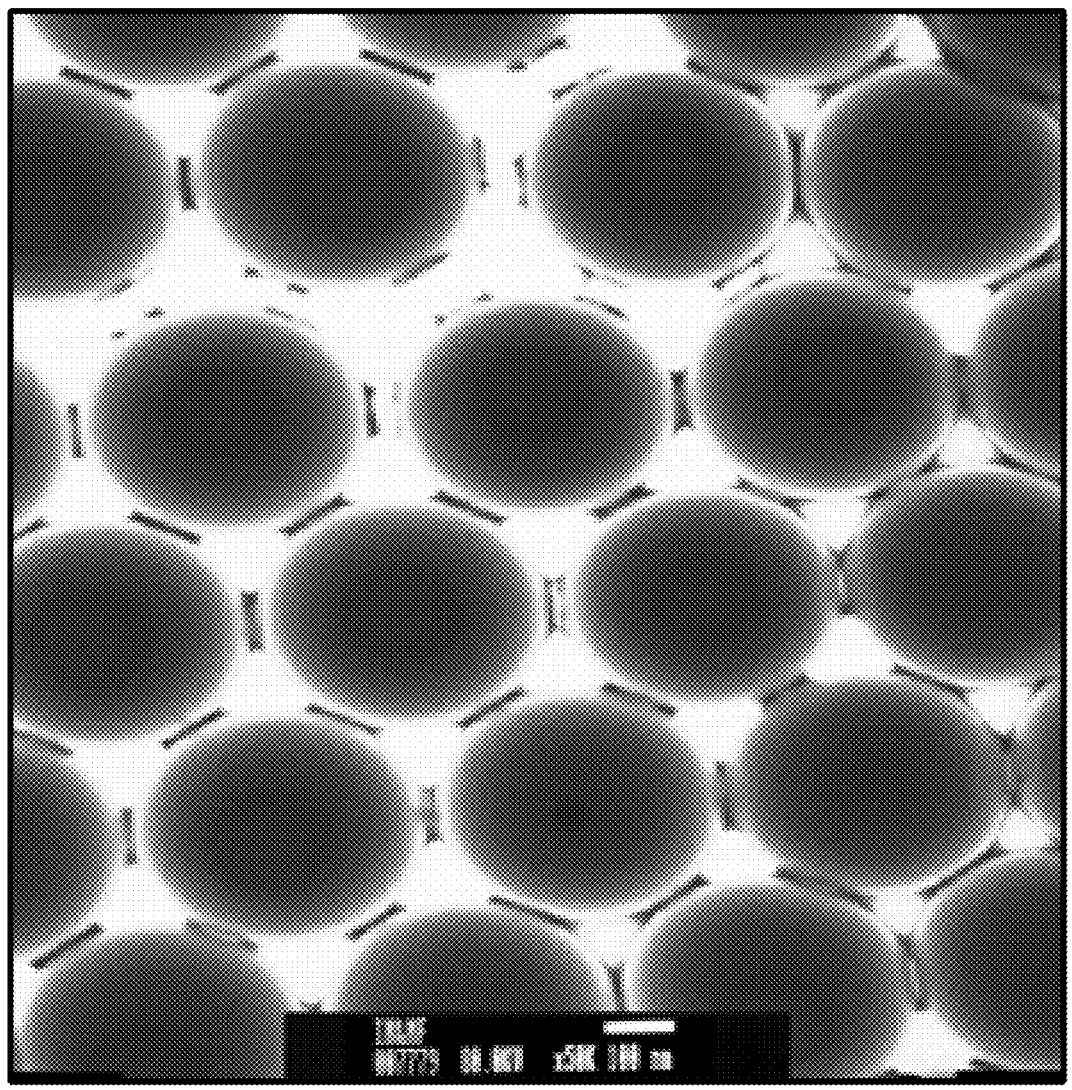
FIG. 2 depicts exemplary gellan gum-b-PEG nanoparticles formed in Example 2 of the present invention.

Gellan-gum-b-PEG-COOH block co-polymer (10 mg/ml) formed in Example 1 was dissolved in deionized water at 30° C. The mixture was added to a 2× volume of tetrahydrofuran while stirring. Stirring was carried out using a homogenizer (PowerGen 700D® homogenizer, Fisher Scientific (Pittsburgh, Pa.)) set at 10,000 rpm for 5 minutes at room temperature. Gellan-gum b-PEG-COOH nanoparticles were recovered by ultracentrifugation at 30,000 rpm for 25 minutes and then dried under vacuum. FIG. 2 provides a view of the formed gellan gum-b-PEG nanoparticles as visualized by a Philips 201 transmission electron microscope (Philips/FEI, Briarcliff, Manor, N.Y.). Particles were visualized following negative staining with 2% w/v uranyl, acetate.

Characterization of Surface Morphology and Size of Nanoparticles:

Test results showed spherical particles with smooth surface (see, FIG. 2). Light scattering study showed a size distribution with a mean hydrodynamic diameter of approximately 250 nm (polydispersity index ~0.5) for the various formulations comprising varying ratios of gellan gum to PEG (F1-F5) studied (Table I). As the results in Table I (below) indicate, the final sizes of these particles seem to be a function of the polymer ratios. For example, as the gellan gum to PEG mass ratio increased from 3:1 to 7:1, a corresponding increase in hydrodynamic diameter of the particles was observed, suggesting increased aggregation with polymer concentrations. An increase in absolute zeta potential with increase in gellan gum to PEG mass ratio up to 5:1 was also observed, and then a decline in zeta potential. The decline in zeta potential at higher polymer ratios may be attributed to the masking of the $COO^-$ on the surface of particles, thus, reducing the surface repulsion. Overall, data showed gellan gum-b-PEG nanoparticles with zeta potential average of −30 mV (average zeta potential of ±30±2 mV; mean±SD, n=5), suggesting the formation of highly stable nanoparticles.

TABLE I

Characterization of fabricated nanoparticles in terms of average mean size and Zeta potential as a function of polymer ratio.

| Sample | Gellan gum:PEG mass ratio | Mean Particle size (nm) | Zeta potential (mV) |
|---|---|---|---|
| F1 | 3:1 | 218 ± 12 | −27.1 |
| F2 | 4.1 | 259 ± 6 | −28.8 |
| F3 | 5:1 | 264 ± 8 | −36.0 |
| F4 | 6:1 | 271 ± 9 | −30.3 |
| F5 | 7:1 | 275 ± 11 | −25.1 |

Note:
All samples were run in triplicate and the data represent the average of the three measurements (mean particle size ± SD).

Nanoparticles were considerably smaller when viewed with TEM than when measured by light scattering technique. This apparent discrepancy in size is attributed to the dehydration of the nanoparticles during sample preparation for TEM imaging. Additionally, light scattering measures the apparent size of a particle, including hydrodynamic layers that form around hydrophilic particles such as those composed of gellan-gum-b-PEG, leading to an overestimation of particle size.

See, for example, Xie et al., *Pharmaceutical Research*, 2005, Vol. 22, pp. 2079-2090, the subject matter of which is hereby incorporated by reference in its entirety.

Zeta potential is a useful indicator of surface charge property and can be employed as an index to the stability of the nanoparticles. See, for example, Cheng et al., *Biomaterials*, 2007, Vol. 28, pp. 869-876, the subject matter of which is hereby incorporated by reference in its entirety. In most cases, the higher the absolute value of the zeta potential of the particles, the larger the amount of charge on their surface. This might result in stronger repellent interactions among the particles, and hence, higher stability of the particles in situ. Our data showed gellan gum-b-PEG nanoparticles with a zeta potential average of about −30 mV (average zeta potential of −30±0.2 mV; mean±SD, n=5). The negative zeta potential observed in gellan gum-b-PEG-COOH nanoparticles is attributed to the presence of free carboxyl moieties on the surface of the particles. The hydrophilic properties of the carboxyl groups on the surface of the particles is considered beneficial in several ways, namely, (i) prevents aggregation of nanoparticles and (ii) offers vast opportunities for surface chemistry such as attachment of ligands to further enhance the target ability of formulation.

Figure 3B:
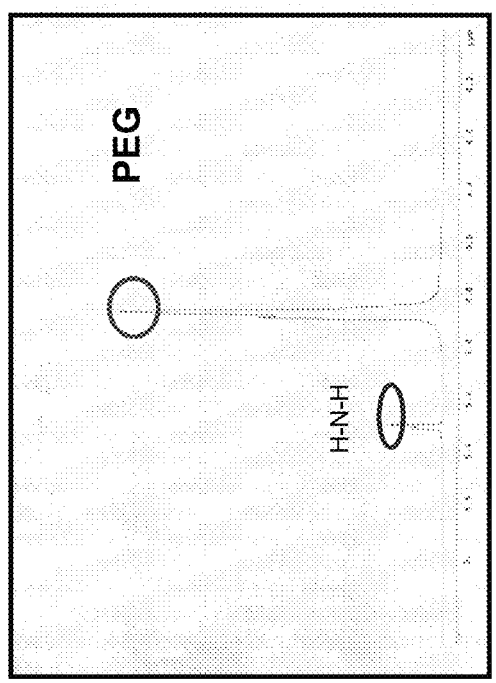
FIGS. 3A-C depict a comparison between the $^1$H-NMR spectrum of (a) gellan gum, (b) $NH_2$—PEG-COOH, and (c) exemplary gellan gum-b-PEG nanoparticles of the present invention.
Figure 3A:
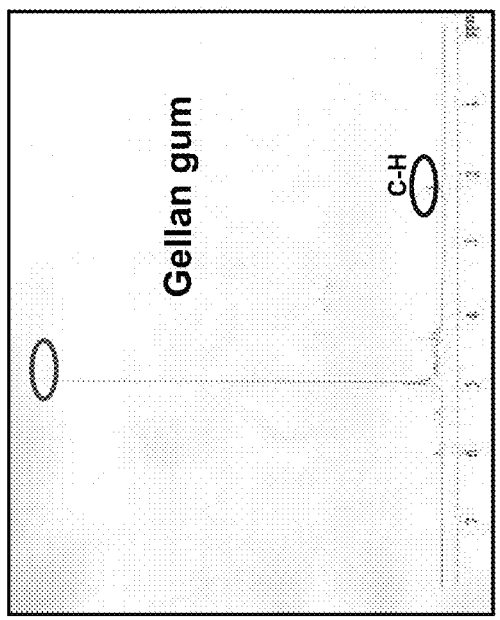
Figure 3C:
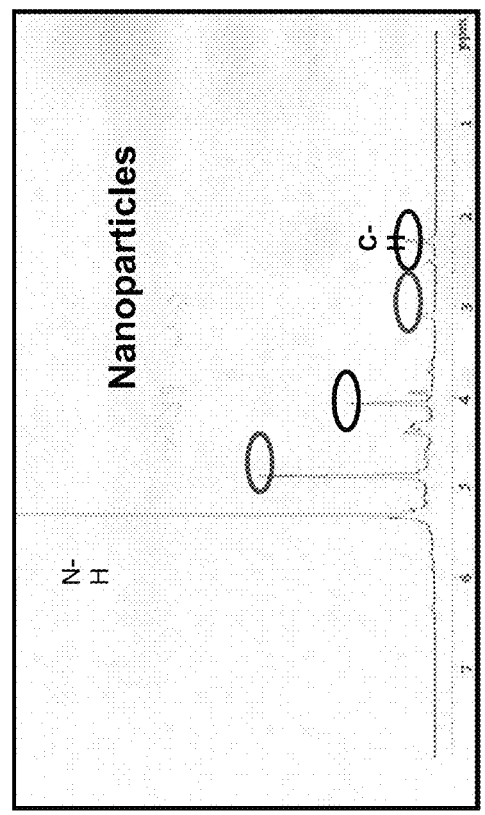

Nuclear Magnetic Resonance Spectroscopy:

FIGS. 3A-3C show the $^1$H-NMR spectrum of (a) gellan gum, (b) $NH_2$—PEG-COOH, and (c) gellan gum-b-PEG nanoparticles respectively. Spectra were obtained following dilution of 1.5 percent of sample in $D_2O$ at 90° C. and recorded using 400 MHz spectrometer equipped with a gradient detection probe and a variable temperature system. The proton of the PEG unit was detected at a peak of 3.71 ppm. The signal at (CH—CN)=2.49 ppm indicated the presence of CN functionality in the formulation. This peak is attributed to the deshielding effect by the electronegativity of the attached nitrogen. In addition, peaks at δ2.26 and 5.2 ppm indicated the presence of CH—CONH and (CO)—NH respectively. Test data revealed that the peak at δ5.2 ppm was a function of the solvent type, as well as concentration of the polymer used. The observed peak at 2.26 ppm was attributed to the deshielding of the α-hydrogen in amides by the carbonyl group. Thus, NMR results provided evidence for the successful linking of gellan gum to an end reactive PEG via amide bond.

Fourier Transform Infrared Spectroscopy (FTIR):

FTIR study was performed to draw information on the crosslinking efficiency between the components of the nanoparticles. FIGS. 4A-4D represent the FTIR spectra of (a) gellan gum, (b) PEG, (c) gellan gum-PEG nanoparticles, and (d) combined spectra respectively. In each case, a 10 mg sample was mixed with potassium bromide and spectra were obtained using Nicolet Impact 410 (Nicolet Analytical Instrument, Madison, Wis.).

In the case of gellan gum alone, a band at 3500 cm$^{-1}$ showed the presence of hydroxyl groups of glucopyranose ring that are hydrogen bonded to various degrees. Carboxyl peaks near 1609 cm$^{-1}$ (symmetric COO— stretching vibration) and 1420 cm$^{-1}$ (asymmetric COO-stretching vibration) were observed to shift slightly to 1604 cm$^{-1}$ and 1415 cm$^{-1}$ following copolymerization with PEG. The band at 2195 cm$^{-1}$ was attributed to a stretching vibration of —$CH_2$ group. The spectrum for the heterofunctional PEG showed an amine peak at 1617 cm$^{-1}$, which showed a slight shift following complex formation. The FTIR spectrum for the GGBP nanoparticles showed a band at 3400 cm$^{-1}$ representing the presence of an amide group while the band at the fingerprint region −1604 cm$^{-1}$ was attributed to C=O stretch of the amide bond. $CH_2$—scissoring also occurred as indicated by the presence of a band at 1465 cm$^{-1}$.

Furthermore, the amount of unreacted $NH_2$—PEG-COOH was determined with TNBS reagent as described in the Test Methods section above. An average of 91% conjugation efficiency was obtained (data not shown) and thus, strong evidence for the covalent linkage of gellan gum and $NH_2$—PEG-COOH via amide bonds was provided since the gellan gum-b-PEG copolymer showed little or no primary amino groups. The observed changes following copolymerization process are attributed to the chemical interaction between the carboxyl group of gellan gum and the amine group of PEG.

Figure 5A:
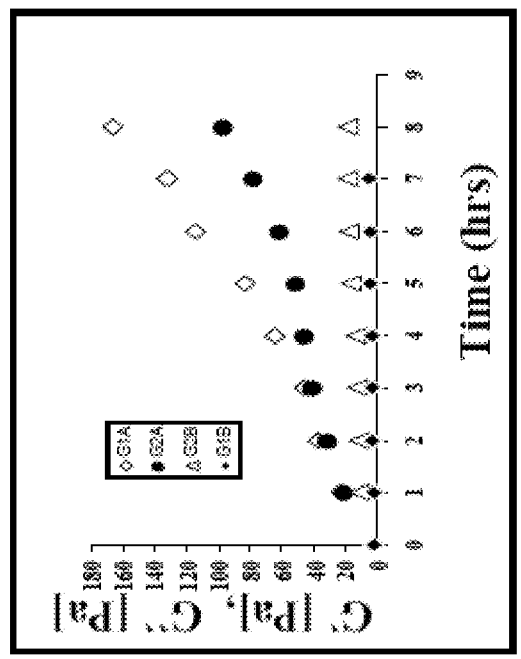
FIGS. 5A-C graphically depict the effect of polymer ratio of gellan gum and PEG on the viscoelastic properties/mechanical strength of exemplary gellan gum-b-PEG nanoparticles of the present invention.
Figure 5B:
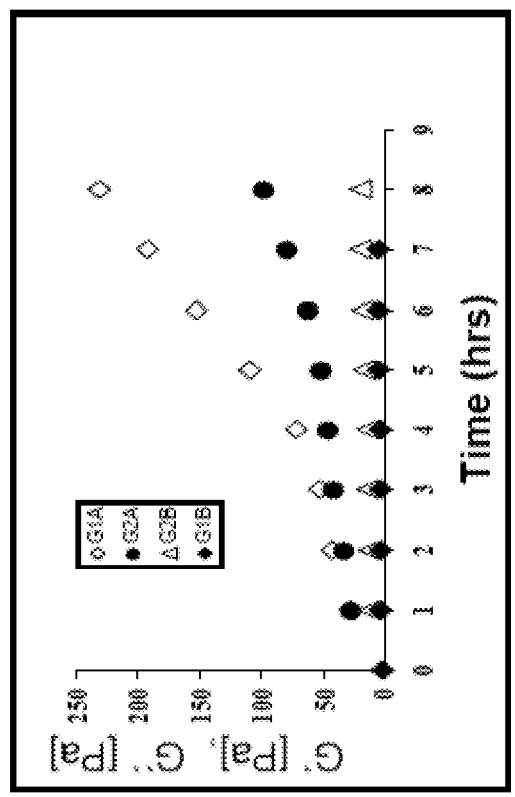
Figure 5C:
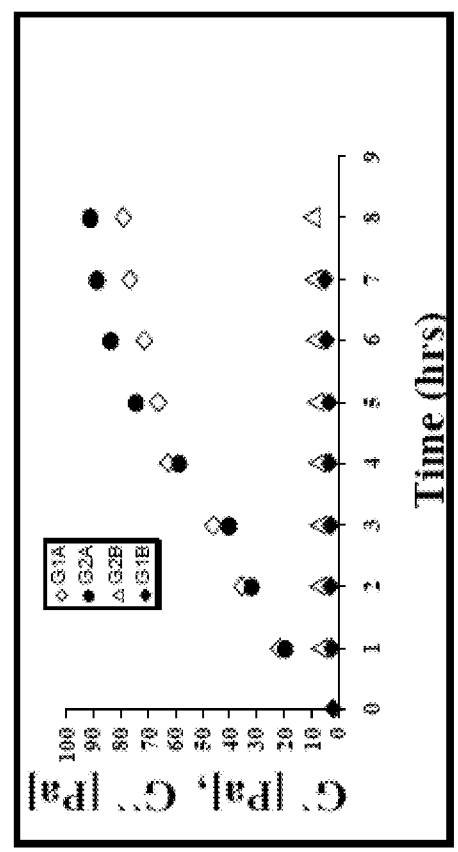

Rheological Studies:

FIGS. 5A-5C show the influence of polymer ratios on the viscoelastic behavior of gellan gum-b-PEG nanoparticles formulation. In FIGS. 5A-5C, the terms G1A and G2A represent the storage modulus (G') and loss modulus (G") of a sample respectively, while the terms G1B and G2B represent the loss modulus (G") and storage modulus (G') of pure gellan gum respectively. The oscillatory measurement was performed at 6.283 rad/s (=1 Hz).

As shown in FIGS. 5A-5C, both the elastic (G') and viscosity (G") complexes of all the samples studied were higher compared to the control. For example, gellan gum to PEG mass ratio of 5:1 resulted in a viscosity increase of about 30 fold compared to the control group (FIG. 5A). A similar trend was observed at polymer ratio of 2:1 (FIG. 5B), however, at gellan gum to PEG mass ratio of 1:5 (FIG. 5C), a loss tangent (tan δ) greater than one was obtained (i.e., observed by the crossover point between G' and G" in FIG. 5C), suggesting a formulation that starts as a gel and begins to turn to fluid after ~5 h. At cross over points, the polymer has as much elastic as viscous components. However, the formulation under consideration has shown the potential to act as a hydrogel in situ and ultimately will result in increased residence time of the encapsulated drug.

Figure 6:
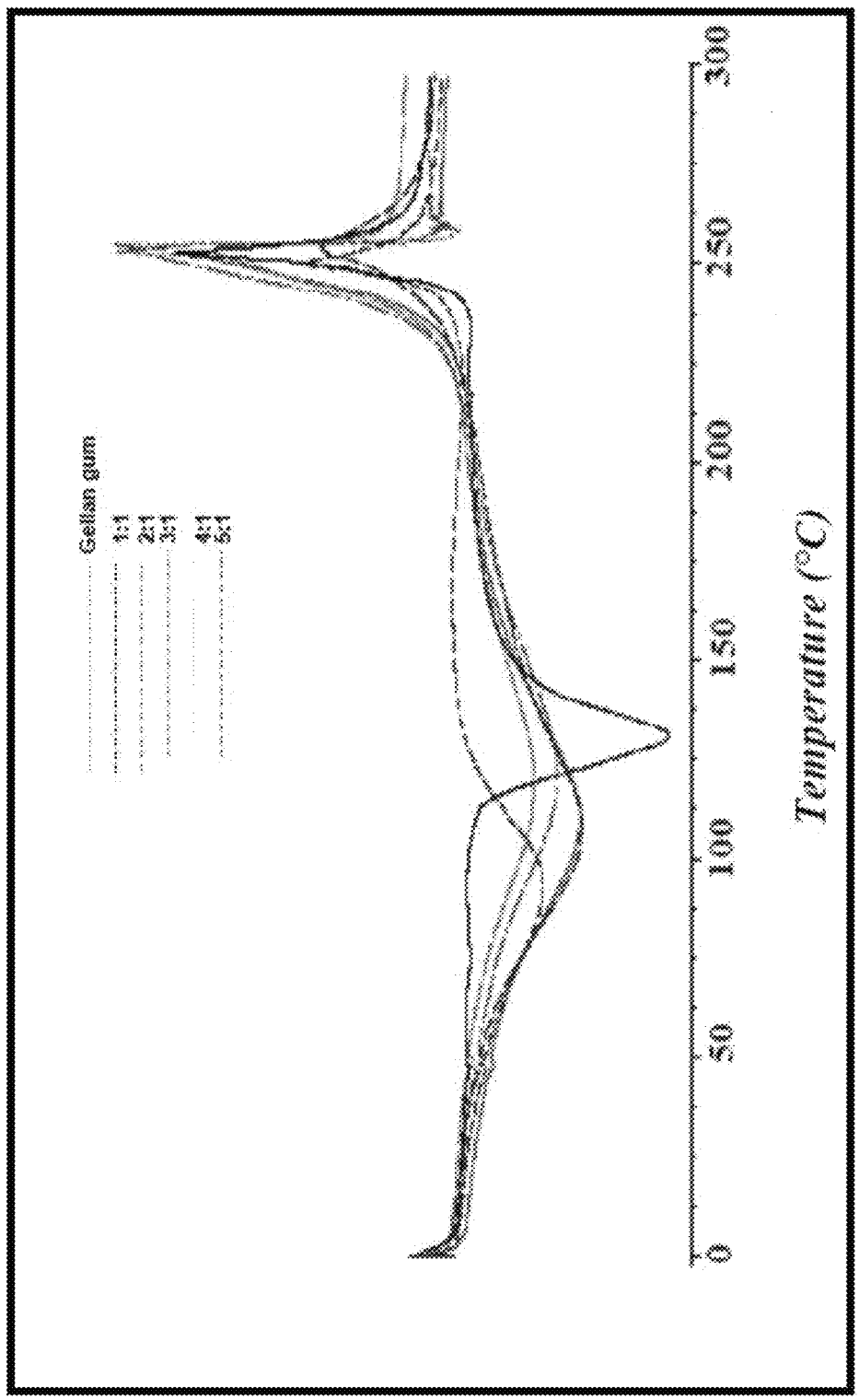
FIG. 6 graphically depicts the effect of polymer ratio of gellan gum and PEG on the thermal stability of gellan gum-b-PEG nanoparticles of the present invention.

Determination of Thermal Stability by Differential Scanning Calorimetry (DSC):

Differential scanning calorimetry is an important technique used in evaluating the thermal stability of particles. FIG. 6 shows the effect of polymer mass ratio of gellan gum and PEG on the thermal behavior of the gellan gum-b-PEG nanoparticles. A temperature range of between 0° C. and 300° C. and a scanning rate of 5° C./min was used in the analysis. Nitrogen was used for purging the sample holders at a flow rate of 20 ml/min.

Result indicated that polymer ratio affected the thermal stability of gellan gum formulation (see FIG. 6 and Table II below). This was evident as the curves showed a characteristic increase in endothermic peak from 70-110° C., which was attributed to the loss of crystalline water molecules during the drying process. The observed exothermic peak at about 250° C. corresponded to the temperature at which disintegration of the molecular chains of the gellan gum-b-PEG nanoparticles formulations occurred.

TABLE II

Peak temperatures and enthalpy changes in the DSC thermograms collected from samples of gellan gum/PEG with different polymer ratios

| Gellan gum:PEG | Temperature (° C.) | | | |
|---|---|---|---|---|
| Polymer ratio | Onset | Peak | Endset | ΔH (J/g) |
| Gellan gum | 71.21 | 95.88 | 114.81 | 43.77 |
|  | 245.26 | 250.03 | 270.54 | 57.81 |
| 1:1 | 84.94 | 108.66 | 133.06 | 48.75 |
|  | 245.63 | 253.44 | 267.99 | 59.27 |

TABLE II-continued

Peak temperatures and enthalpy changes in the DSC thermograms collected from samples of gellan gum/PEG with different polymer ratios

| Gellan gum:PEG Polymer ratio | Temperature (° C.) | | | ΔH (J/g) |
|---|---|---|---|---|
| | Onset | Peak | Endset | |
| 2:1 | 82.60 | 111.63 | 139.42 | 67.71 |
|  | 249.22 | 254.53 | 260.35 | 118.0 |
| 3:1 | 91.68 | 116.75 | 138.58 | 25.22 |
|  | 238.07 | 253.30 | 261.20 | 96.72 |
| 4:1 | 93.64 | 121.95 | 149.18 | 49.00 |
|  | 236.07 | 253.31 | 257.81 | 154.00 |
| 5:1 | 116.19 | 130.97 | 150.46 | 134.00 |
|  | 248.63 | 252.54 | 263.32 | 73.69 |

Figure 7:
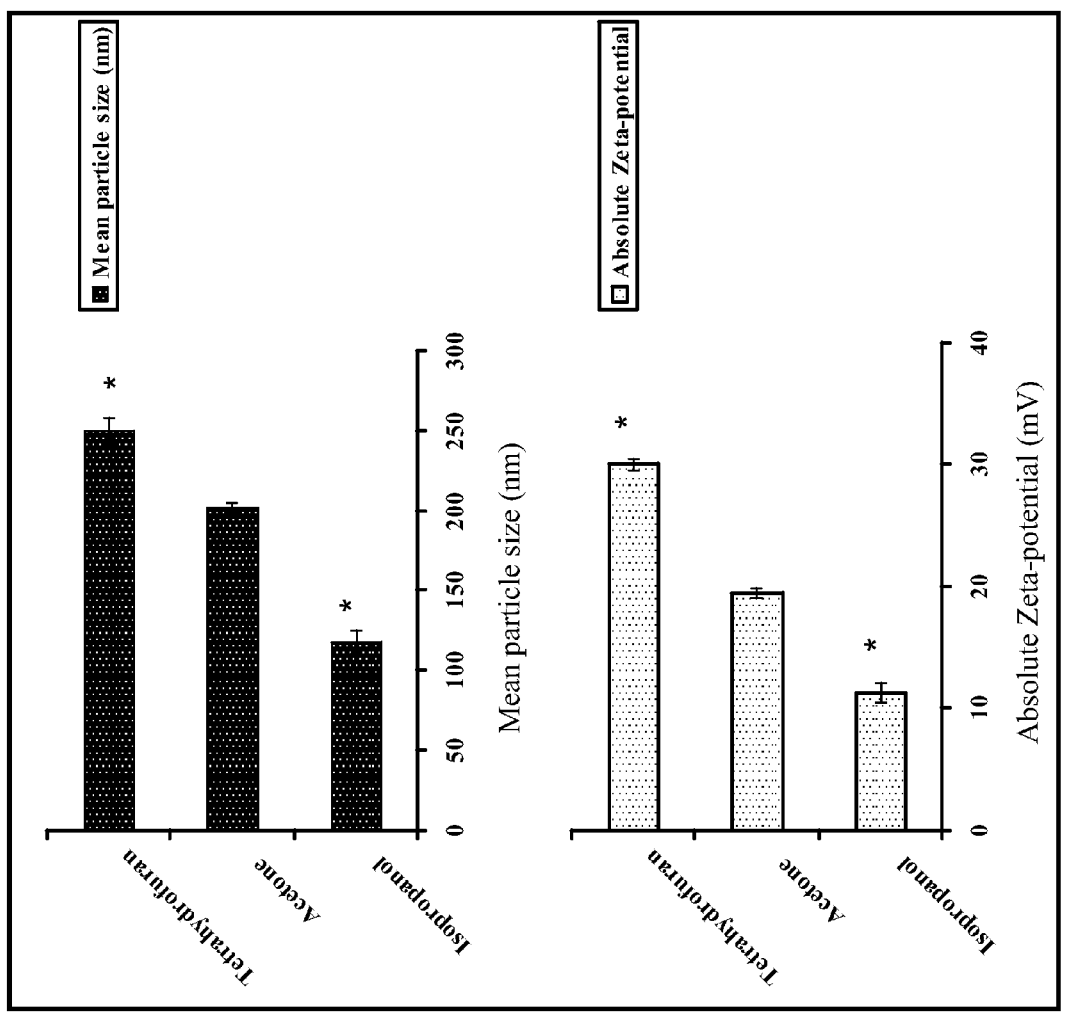
FIG. 7 graphically depicts the effect of solvent choice on particle size (nm) and zeta potential (mV) of gellan gum-b-PEG nanoparticles of the present invention.

Effect of Solvent on Nanoparticle Particle Size:

FIG. 7 graphically depicts the effect of solvent choice on particle size (nm) and zeta potential (mV) of gellan gum-b-PEG nanoparticles of the present invention. Parameters such as water ratio, polymer ratio, and stirring speed were kept constant for a given solvent. Each experiment was repeated twice and values represent the average of two separate studies. In FIG. 7, the * symbol represents p-value of isopropanol as solvent compared to tetrahydrofuran. As mentioned above, $p<0.05$ is considered statistically significant.

Figure 8:
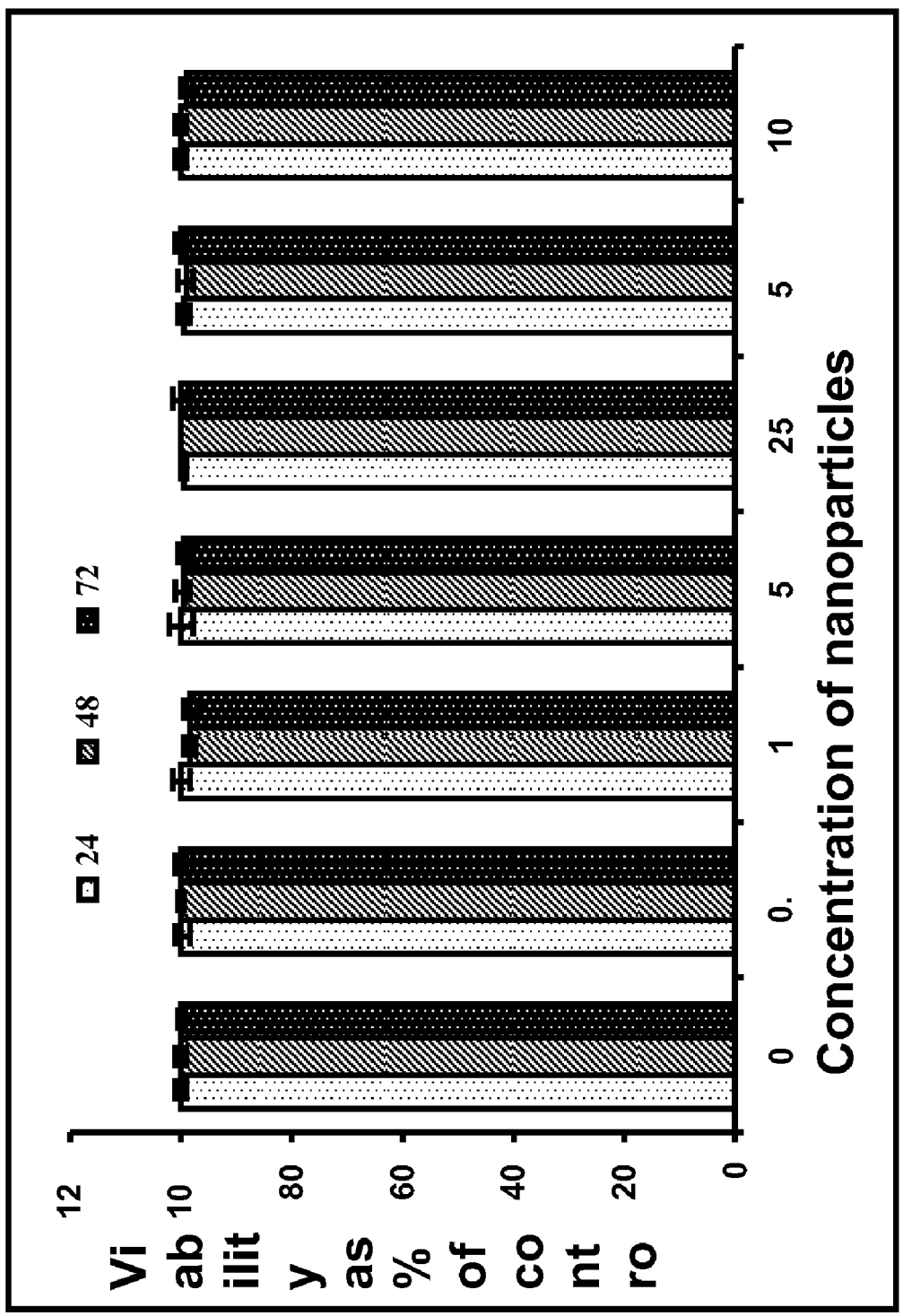
FIG. 8 graphically depicts the effect of gellan gum-b-PEG nanoparticles of the present invention on activated human T-cells.

Effect of Nanoparticles on Activated Human T-Cells:

FIG. 8 shows the effect of gellan gum-b-PEG nanoparticles on activated human T-cells, which represent a model eukaryotic system. Cells were exposed to the growth medium containing varying concentrations (0.1-100 mg/ml) of gellan gum-b-PEG nanoparticles and further incubated for 24 h, 42 h and 72 h periods. At the end of the incubation period, cells were harvested and counted using hemacytometer. Data provided is a representation of three independent experiments.

As shown in FIG. 8, no apparent difference in cell viability of the treated groups compared to the untreated control was observed. This observation was consistent for the various time points studied; for example, cell viability after 24 h, 48 h and 72 h exposure to 100 mg/ml of nanoparticles were 100%, 100% and 98.9% respectively, suggesting the safety of gellan gum-b-PEG nanoparticles for use as drug delivery vehicles.

Uptake and Localization of Nanoparticles in Human Prostate Cancer Cells:

Nano-sized particles (other than gellan gum-b-PEG nanoparticles) have been shown as effective delivery agents for certain drugs. Therefore, to evaluate the efficiency of gellan gum-b-PEG nanoparticles as potential anticancer drug delivery agents, their cellular uptake and localization using confocal microscopy, human prostate cancer cell line (PC-3) was investigated. In this experiment, formulated nanoparticles were stained with a fluorescent dye, BSA-FITC, as described in the Test Methods section above.

Figure 9A:
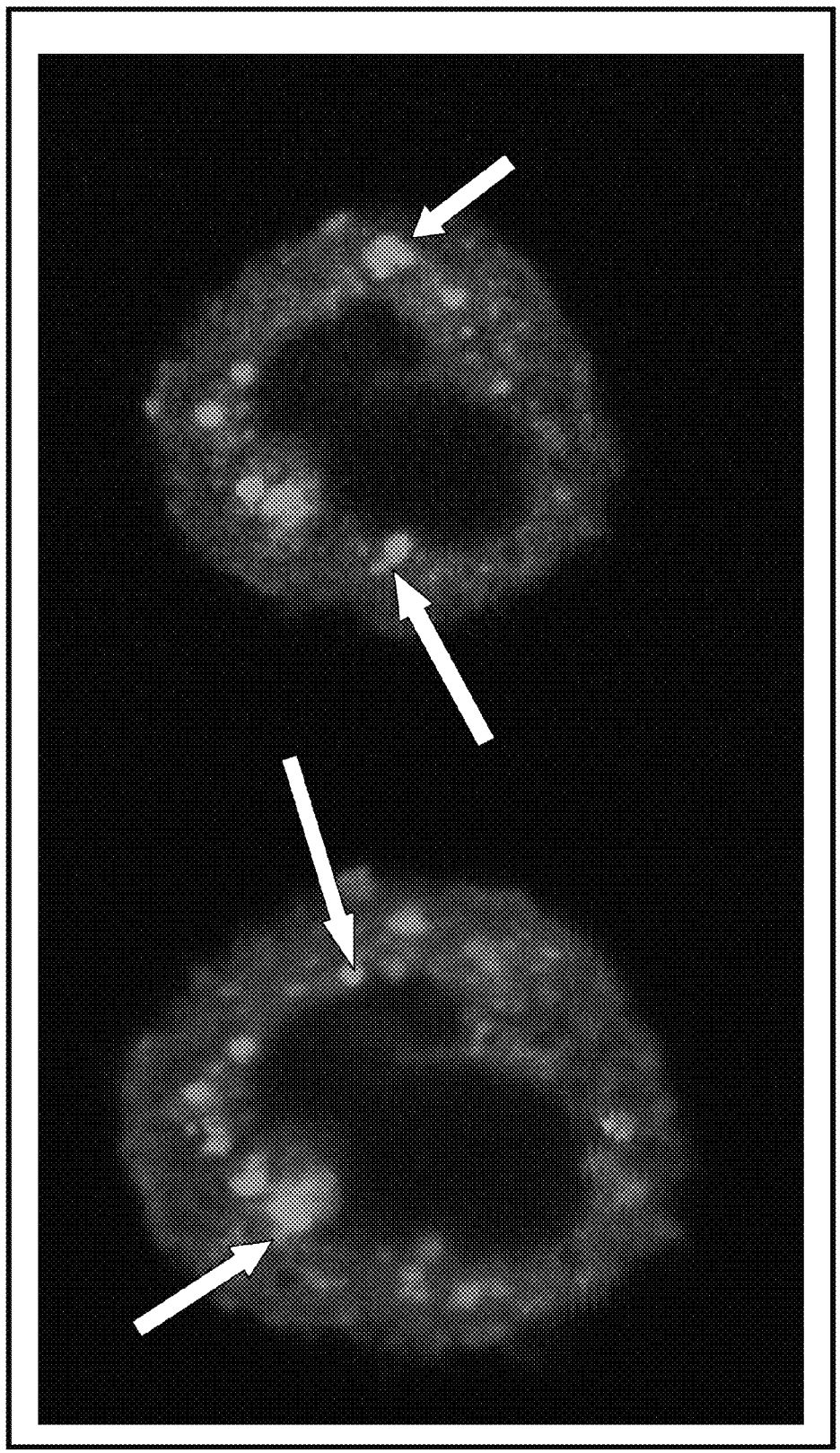
FIGS. 9A-9C depict the uptake and localization of gellan gum-b-PEG nanoparticles in human prostate carcinoma cells (PC-3)
Figures 9B, 9C:
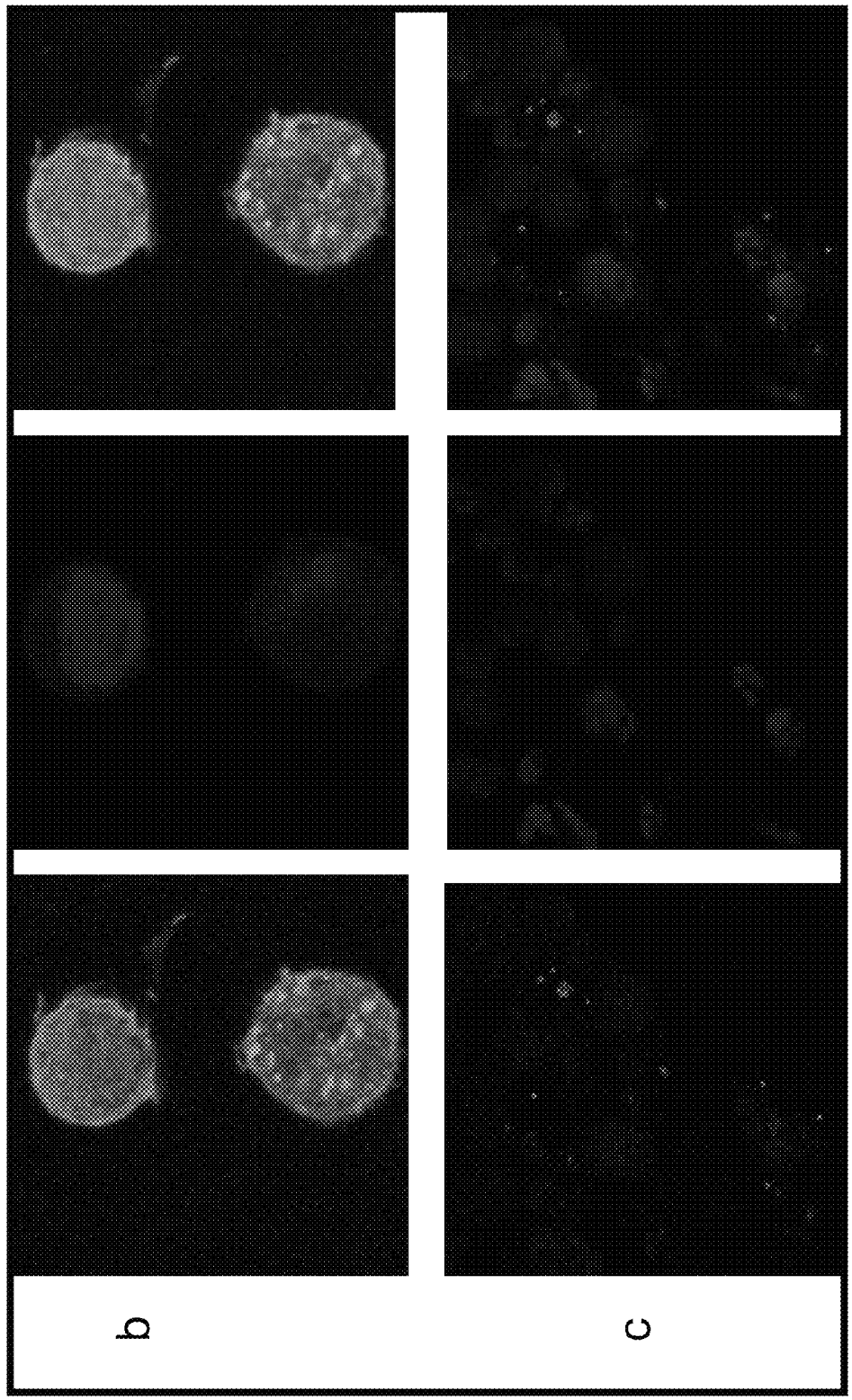

FIGS. 9A-9C provide evidence of uptake and localization of gellan gum-b-PEG nanoparticles by human prostate cancer cells. FIG. 9A and FIG. 9B (i.e., the upper row of figures designated "b") showed that nanoparticles were taken up by the cancer cells within 2 h of incubation. In order to exclude the possibility of nonspecific staining of cells by BSA-FITC, the supernatant of BSA-FITC nanoparticles shaken for 2 h and centrifuged twice was incubated with the cells to check for any leakage of dye from the nanoparticles, which might stain cells. No fluorescence was detected in the cells (see, FIG. 9C, the lower row of figures designated "c"). This data indicated that the fluorescent dye did not leak from the particles into the cell membrane, but rather particles was taken up by the cells and that these cells were mostly localized to the cytosol.

As described above, gellan gum-b-PEG-COOH nanoparticles were successfully formulated and data showed that the gellan gum-b-PEG-COOH nanoparticles of the present invention can effectively deliver active molecules, such as anti-cancer drugs, to target sites without affecting the activities of normal human cells.

Example 3

Formulation of Functionalized Gellan Gum-b-PEG-Apt Nanoparticles

The surfaces of GGbPEG copolymeric nanoparticles were functionalized by attaching an RNA-aptamer ligand that is specific for human prostate specific membrane antigen (PSMA). The process of ligand attachment was carried out as follows.

GGbPEG nanoparticles (10 mg/ml) of Example 2 were suspended in double deionized water and incubated with EDC (300 mM) and NHS (150 mM) for 20 min. Nanoparticles were then repeatedly washed in DNase-, RNase-free deionized water followed by ultrafiltration. The NHS-activated nanoparticles were reacted with 50-amino-RNA aptamer (1 mg/mL). The resulting nanoparticle-aptamer bioconjugates (GGbPEG-Apt) were washed with ultrapure water (15 ml) by ultrafiltration, and the surface-bound aptamer were denatured at 90° C. and allowed to assume binding conformation during snap-cooling on ice. The nanoparticles suspensions were kept at 4° C. until use.

Figure 10A:
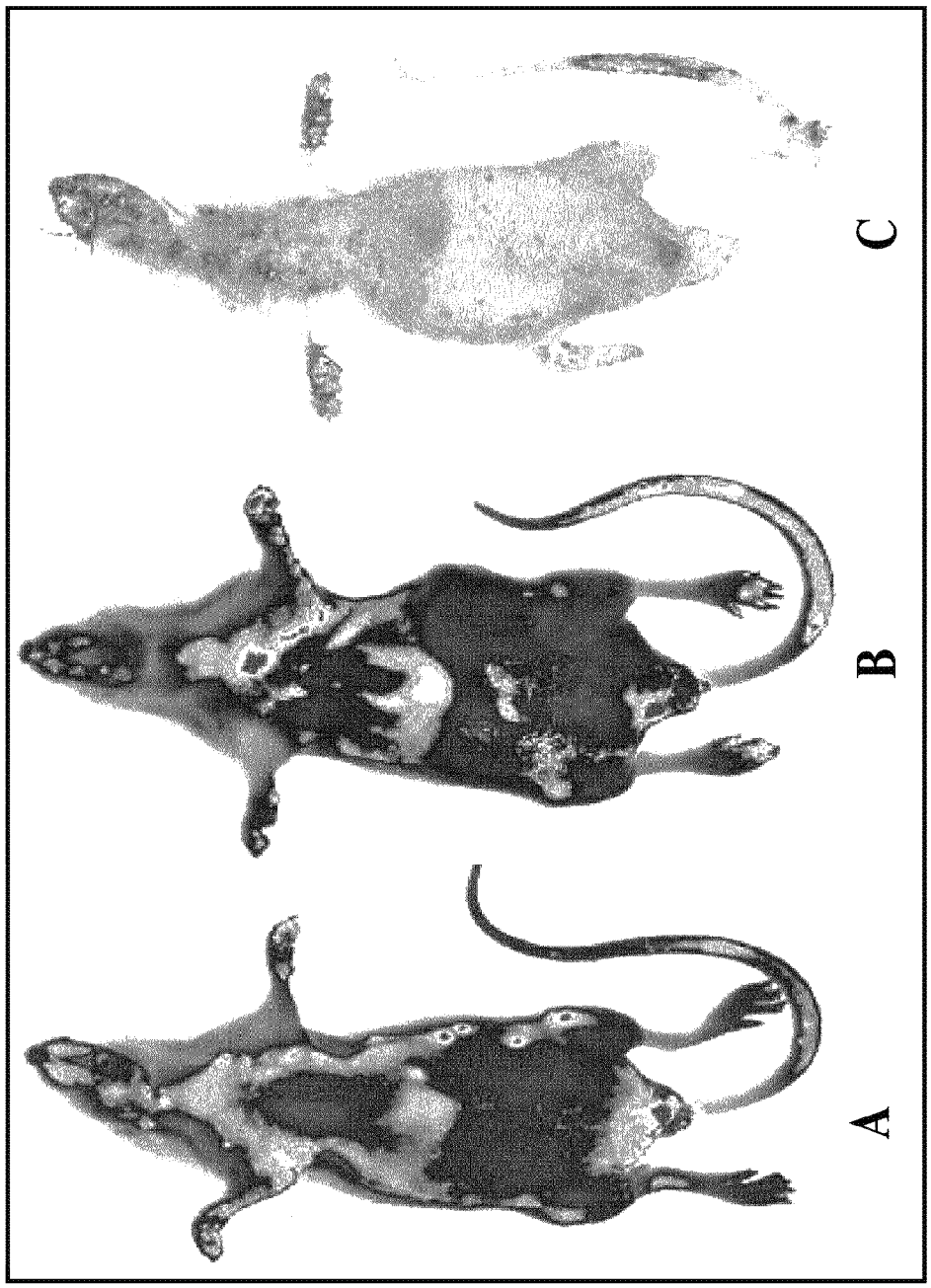
FIGS. 10A-10C depict in vivo biodistribution of functionalized fluorescent GGbPEG copolymeric nanoparticles in athymic nude mice bearing human xenograft of prostate tumor.
Figure 10B:
Figure 10C:
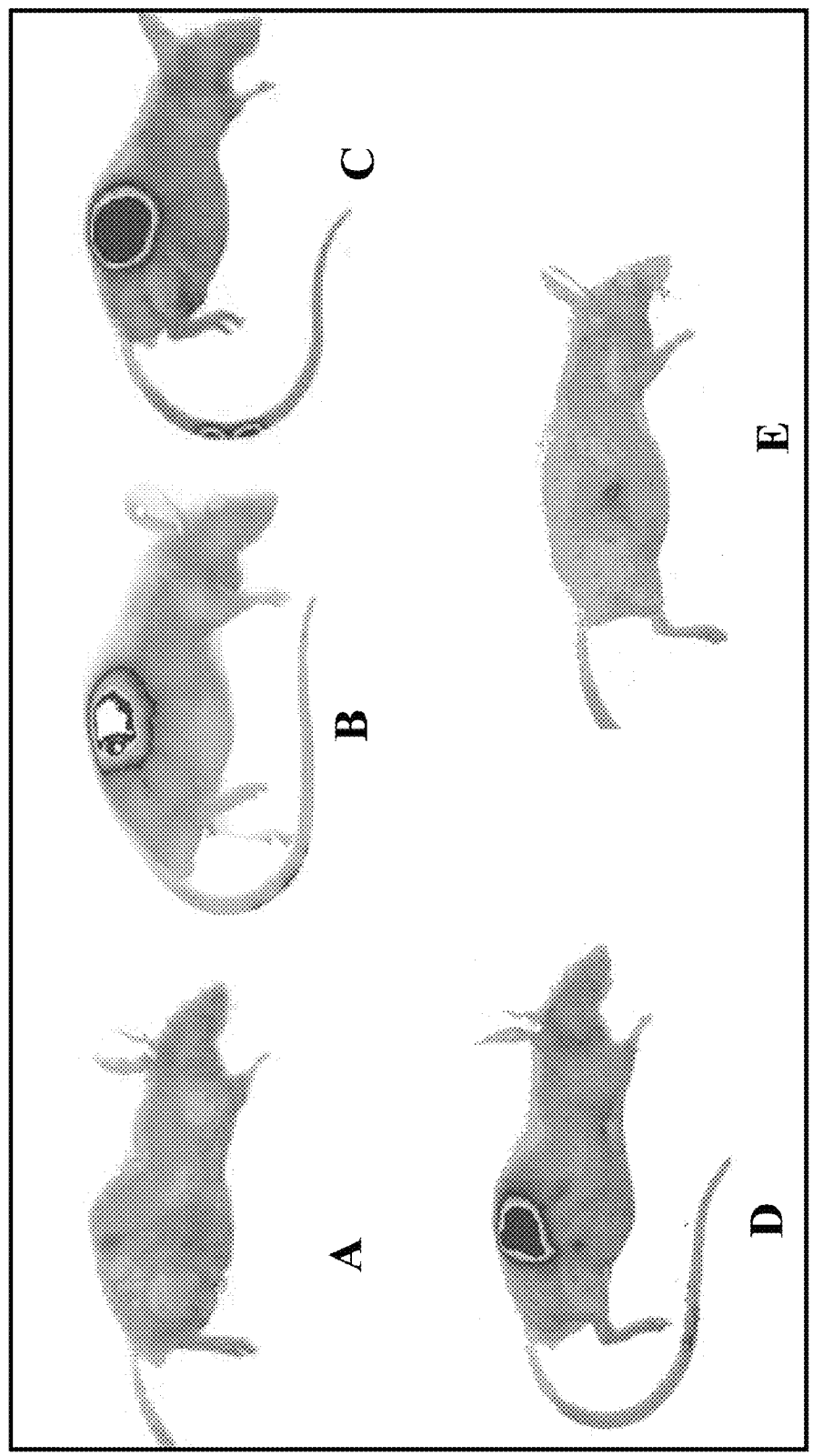

In vivo Biodistribution of Functionalized GGbPEG Copolymeric Nanoparticles:

FIGS. 10A-10C depict in vivo biodistribution of functionalized fluorescent GGbPEG copolymeric nanoparticles in athymic nude mice bearing human xenograft of prostate tumor. FIG. 10A depicts IR-Dye 800 CW treated mice with A, B and C representing 6 h, 24 h and 48 h post treatment respectively. FIG. 10B depicts mice treated with fluorescent-labeled GGbPEG nanoparticles with A=saline treated, B=IR-Dye 800 CW-loaded GGbPEG nanoparticles (24 h post injection), and C=IR-Dye 800 CW-loaded GGbPEG nanoparticles (96 h post injection). FIG. 10C depicts mice treated with fluorescent-labeled aptamer-GGbPEG nanoparticles with A=saline treated, B=24 h post injection, C=96 h post injection, D=14 days post injection, and E=21 days post injection.

As shown FIGS. 10A-10C, increased accumulation of aptamerized fluorescent nanoparticles was observed for up three weeks in mice treated with IR dye-800 CW-loaded GGbPEG-aptamer nanoparticles (FIG. 10C) compared to less than 96 h residence time observed in mice treated with fluorescent nanoparticles alone (FIG. 10B). On the other hand, mice treated with saline or IR-Dye 800 CW alone (FIG. 10A) showed in vivo clearance within 48 h post injection, suggesting the ability of surface functionalized GGbPEG nanoparticles to improve the residence time of the encapsulated drug. The ability of the aptamer-GGbPEG fluorescein nanoparticles to maintain a significantly higher concentration in the tumor over prolonged time interval may be attributed to uptake by the targeted tumor cells.

Example 4

Formulation of Ptx-Loaded GGbPEG Nanoparticles

Ptx-loaded GGbPEG copolymeric nanoparticles were prepared as follows. GGbPEG co-polymer (10 mg/ml) of Example 2 was dissolved in double deionized water at 30° C. and mixed with various concentrations of Ptx (1-5% w/w) in tetrahydrofuran, and then the mixture was added to a 2× volume of stirring tetrahydrofuran. Stirring was carried out using a homogenizer (PowerGen 700D®homogenizer) set at 10,000 rpm for 15 minutes at room temperature. Ptx-loaded GGbPEG nanoparticles (Ptx-GGbPEG nanoparticles) were recovered via filtration through a 0.22 µm filter and ultracentrifugation at 30,000 rpm for 25 minutes. The recovered drug-loaded nanoparticles were dried under vacuum and used without further treatments.

Example 5

Formulation of Surface Functionalized Ptx-GGbPEG Copolymeric Nanoparticles

The surfaces of Ptx-GGbPEG copolymeric nanoparticles were functionalized by attaching an RNA-aptamer ligand that is specific for human prostate specific membrane antigen (PSMA). The process of ligand attachment was carried out as follows.

Ptx-GGbPEG nanoparticles (10 mg/ml) of Example 4 were suspended in double deionized water and incubated with EDC (300 mM) and NHS (150 mM) for 20 min. Nanoparticles were then repeatedly washed in DNase-, RNase-free deionized water followed by ultrafiltration. The NHS-activated nanoparticles were reacted with 50-amino-RNA Apt (1 mg/mL). The resulting loaded nanoparticle-aptamer bioconjugates (Ptx-GGbPEG-Apt) were washed with ultrapure water (15 ml) by ultrafiltration, and the surface-bound aptamer were denatured at 90° C. and allowed to assume binding conformation during snap-cooling on ice. The nanoparticles suspensions were kept at 4° C. until use.

Figure 11:
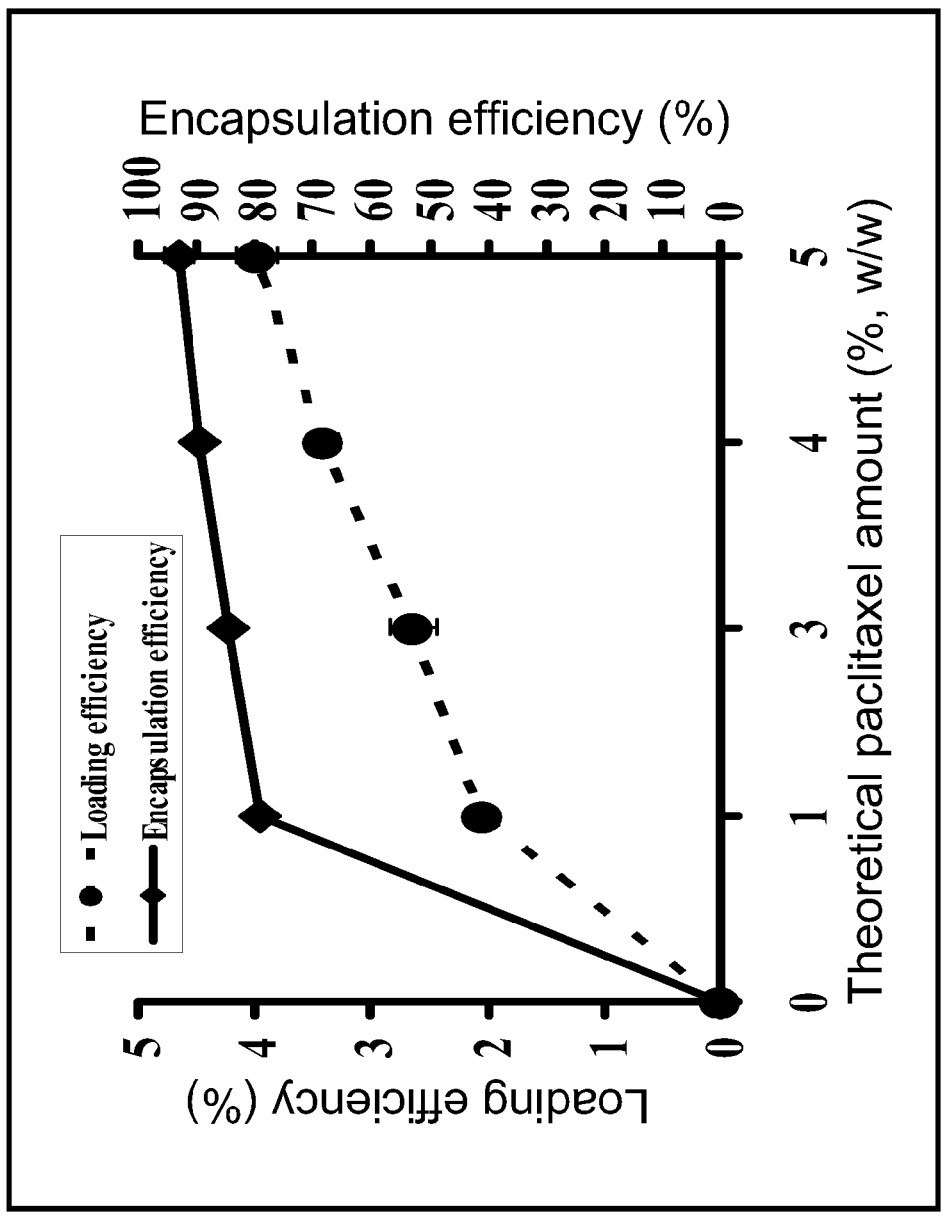
FIG. 11 graphically depicts the effect of theoretical dose of paclitaxel (Ptx) on the loading and encapsulation efficiency of Ptx-loaded GGbPEG nanoparticles.

Determination of Ptx Content in the Nanoparticles:

FIG. 11 shows the effect of theoretical Ptx content on the loading and encapsulation efficiencies of Ptx-GGbPEG nanoparticles prepared by nanoprecipitation. The results shown in FIG. 11 indicates that a loading efficiency of about 4% (w/w) and an encapsulation efficiency of 93% (w/w) can be achieved simultaneously when the theoretical drug content is 5% (w/w). The results show that Ptx-GGbPEG nanoparticles with high loading and encapsulation efficiencies can be obtained simultaneously by nanoprecipitation.

Figure 12:
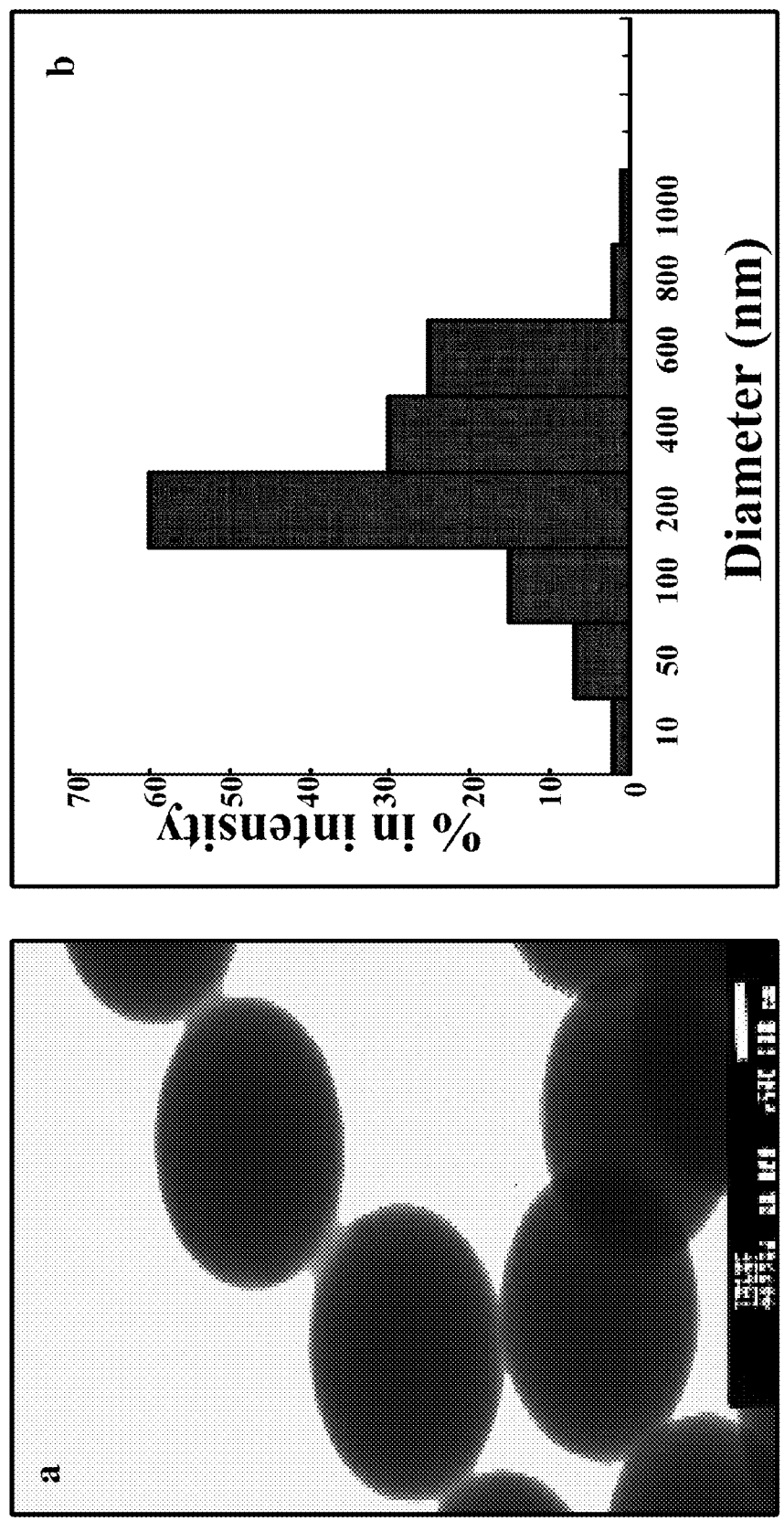
FIG. 12 depicts (a) TEM microphotograph of Ptx-loaded GGbPEG nanoparticles as visualized by Philips 201 transmission electron microscope, and (b) particle size distribution of Ptx-loaded nanoparticles as observed by dynamic light scattering.

Surface Morphology, Charge and Particle Size of Ptx-Loaded Nanoparticles:

Morphological examination of Ptx-GGbPEG nanoparticles by TEM and dynamic light scattering revealed spherical nano-sized particles with an average particle size of 300±52 nm (see FIG. 12 components "a" and "b" respectively). Furthermore, data obtained by dynamic light scattering indicated that the content of paclitaxel in the particles considerably affected the particle size, but did not affect the surface charge (zeta potential) of the particles. This indicated that the drug was encapsulated in the nanoparticles rather than adsorbed on the surface, thus, no significant change in surface charges (zeta potential) was observed.

Figure 13:
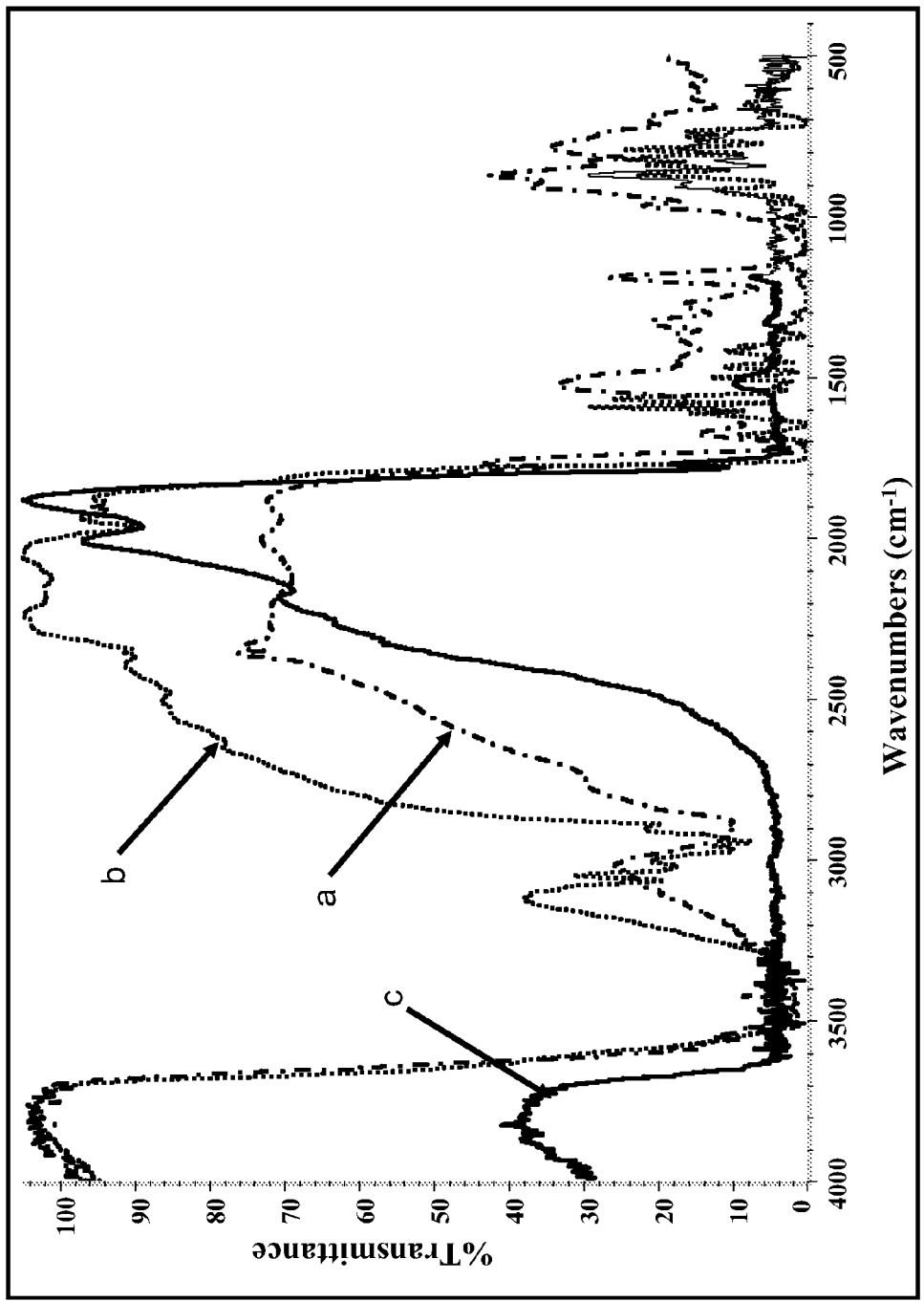
FIG. 13 depicts FTIR spectra of (a) GGbPEG copolymeric nanoparticles, (b) paclitaxel (Ptx) alone, and (c) Ptx-loaded GGbPEG nanoparticles.

FT-IR Spectroscopy:

The FT-IR spectra of GGbPEG copolymeric nanoparticles (FIG. 13, designation "a"), Ptx alone (FIG. 13, designation "b"), and Ptx-GGbPEG nanoparticles (FIG. 13, designation "c") are shown in FIG. 13. The FTIR spectrum for the GGbPEG nanoparticles (FIG. 13, designation "a") shows a band at 3400 $cm^{-1}$ representing the presence of an amide group while the band at the fingerprint region 1604 $cm^{-1}$ is attributed to C=O stretch of the amide bond. $CH_2$ scissoring also occurred as indicated by the presence of a band at 1465 $cm^{-1}$.

The spectrum of Ptx shows strong absorption bands in the range of 1750-1600, 1300-1180, and 770-630 $cm^{-1}$ (FIG. 13, designation "b"). Furthermore, the spectrum for the Ptx-GGbPEG nanoparticles (FIG. 13, designation "c") shows the presence of residual moisture content resulting in a broad peak from 3500-2800 $cm^{-1}$. The spectrum also shows the peak representing $CH_2$ scissoring mode of paclitaxel at 1411 $cm^{-1}$. The peak at 1651 $cm^{-1}$, representative of C=O stretch of amide bond in GGbPEG nanoparticles, shifted to 1648 $cm^{-1}$ in the presence of paclitaxel. In addition, the peak due to N—H bending vibration, which was observed at 1589 $cm^{-1}$ in GGbPEG nanoparticles, was lowered both in wavenumber (1579 $cm^{-1}$) and intensity. Presence of few characteristic peaks of paclitaxel was due to possible interference caused by polymers.

Figure 14:
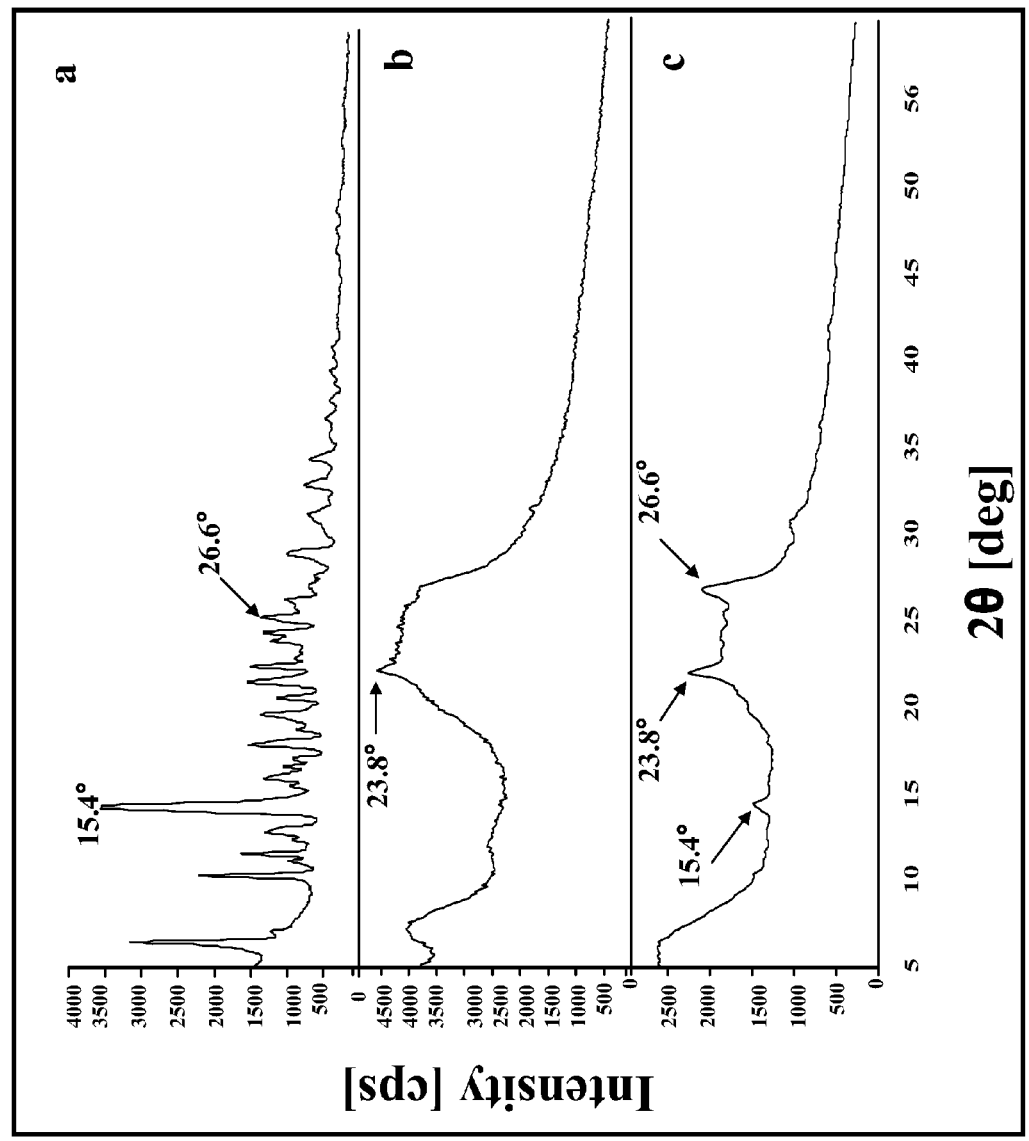
FIG. 14 depicts (a) X-ray powder diffraction patterns of pure Ptx, (b) GGbPEG copolymeric nanoparticles, and (c) Ptx-loaded GGbPEG nanoparticles.

X-ray Diffraction Studies:

X-ray diffraction analysis was performed to determine whether the entrapped Ptx existed in the less water-soluble crystalline state or the more soluble amorphous state. As the results in FIG. 14 indicate, pure Ptx shows a diffractogram consistent with its crystalline nature (FIG. 14, designation "a") since it exhibited several intense characteristic peaks at 2θ=5.6°, 9.9°, 12.7° and 15°, while GGbPEG diffractogram shows amorphous character (FIG. 14, designation "b"). In contrast, the sharp peaks observed in pure Ptx were not visible in the diffraction patterns from samples of Ptx-GGbPEG nanoparticles (FIG. 14, designation "c"), suggesting that the Ptx entrapped in the GGbPEG nanoparticles existed in an amorphous state which provides with increased solubility of the encapsulated Ptx as compared to crystalline state.

Figure 15:
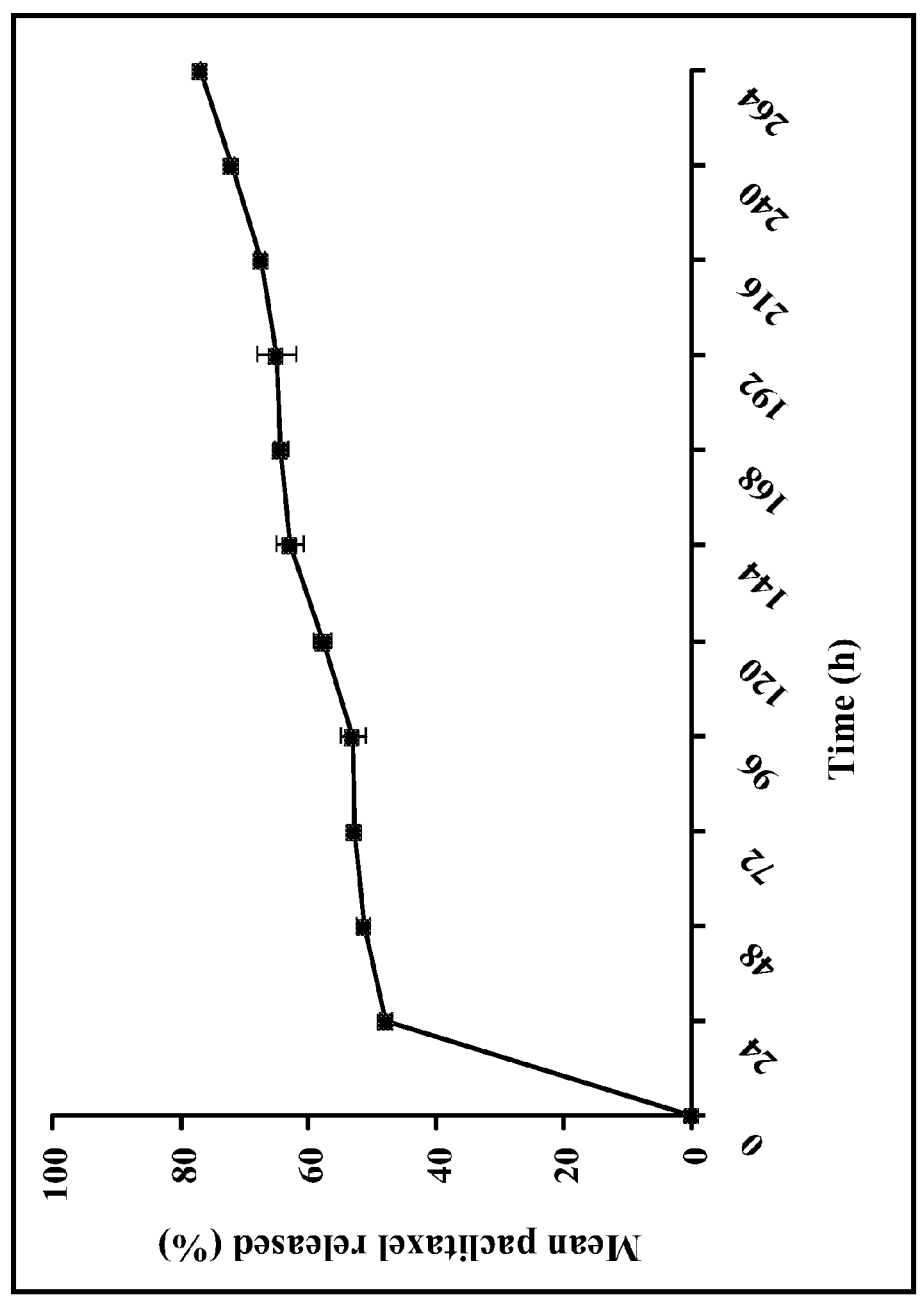
FIG. 15 depicts in vitro mean Ptx release (mean±S.D., n=3) profile for Ptx-loaded GGbPEG copolymeric nanoparticles prepared via nanoprecipitation with drug loading efficiency of 2.87±0.13 (w/w)

In vitro Release Study of Ptx-GGbPEG Nanoparticles:

FIG. 15 shows the mean Ptx release profile from GGbPEG copolymeric nanoparticles. The results demonstrated that Ptx was continuously released from the block copolymer nanoparticles in the aqueous medium containing 1 M sodium salicylate up to eleven days. The mean release amount of Ptx on day eleven was 90.3%. Due to the challenges involved in maintaining a good sink condition while studying the in vitro release profile of poorly water soluble drugs such as Ptx, the drug was solubilized in hydrotropic agents such as sodium salicylate, which provided the opportunity to maintain a continuous flow of the drug into the release media, thus, enabling a more accurate assessment of the release profile.

Figure 16A:
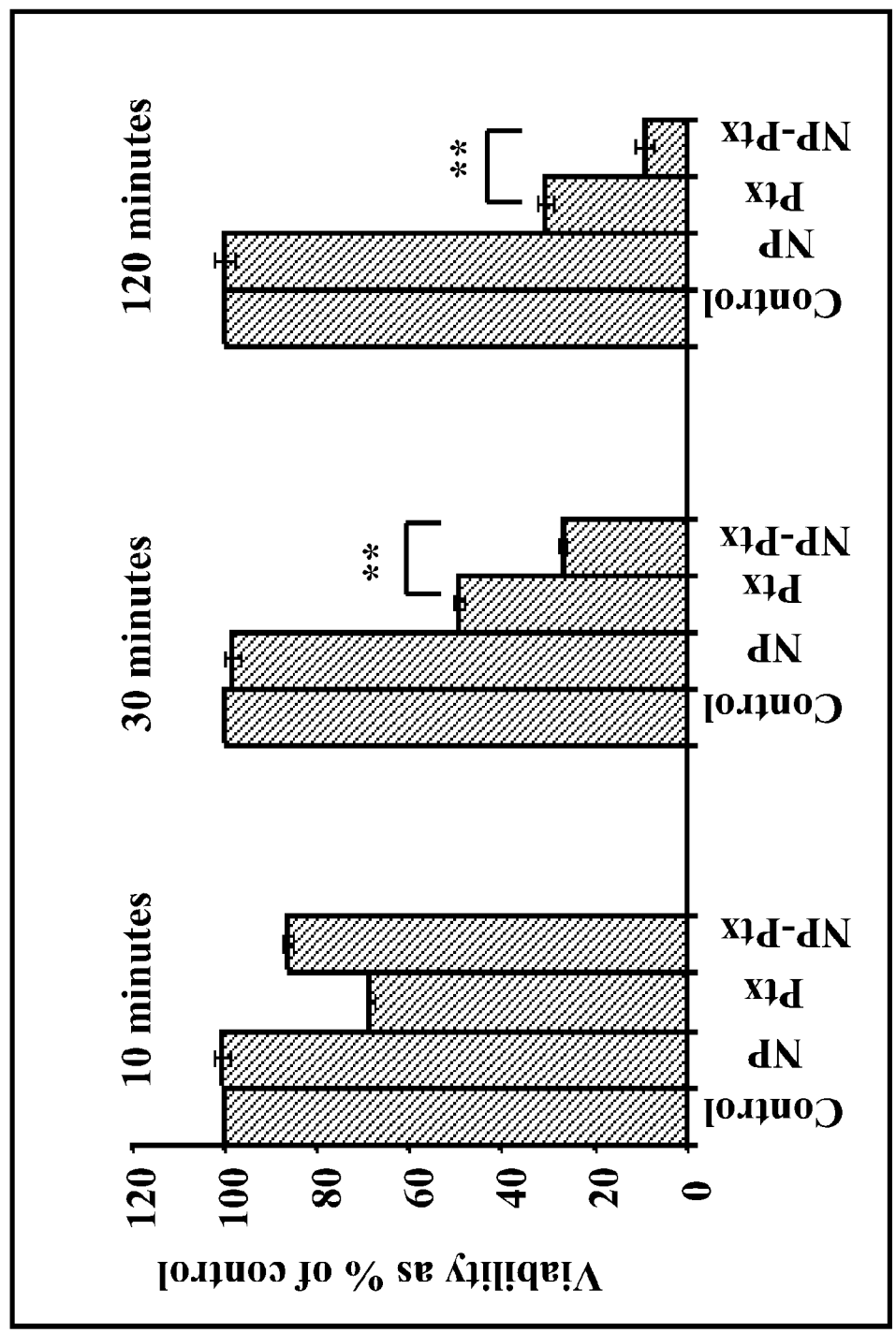
FIGS. 16A-16B depict time-dependent cytotoxic effects of paclitaxel or Paclitaxel-loaded gellan gum-b-PEG nanoparticles on human prostate adenocarcinoma cell lines DU-145 and PC-3 respectively.
Figure 16B:
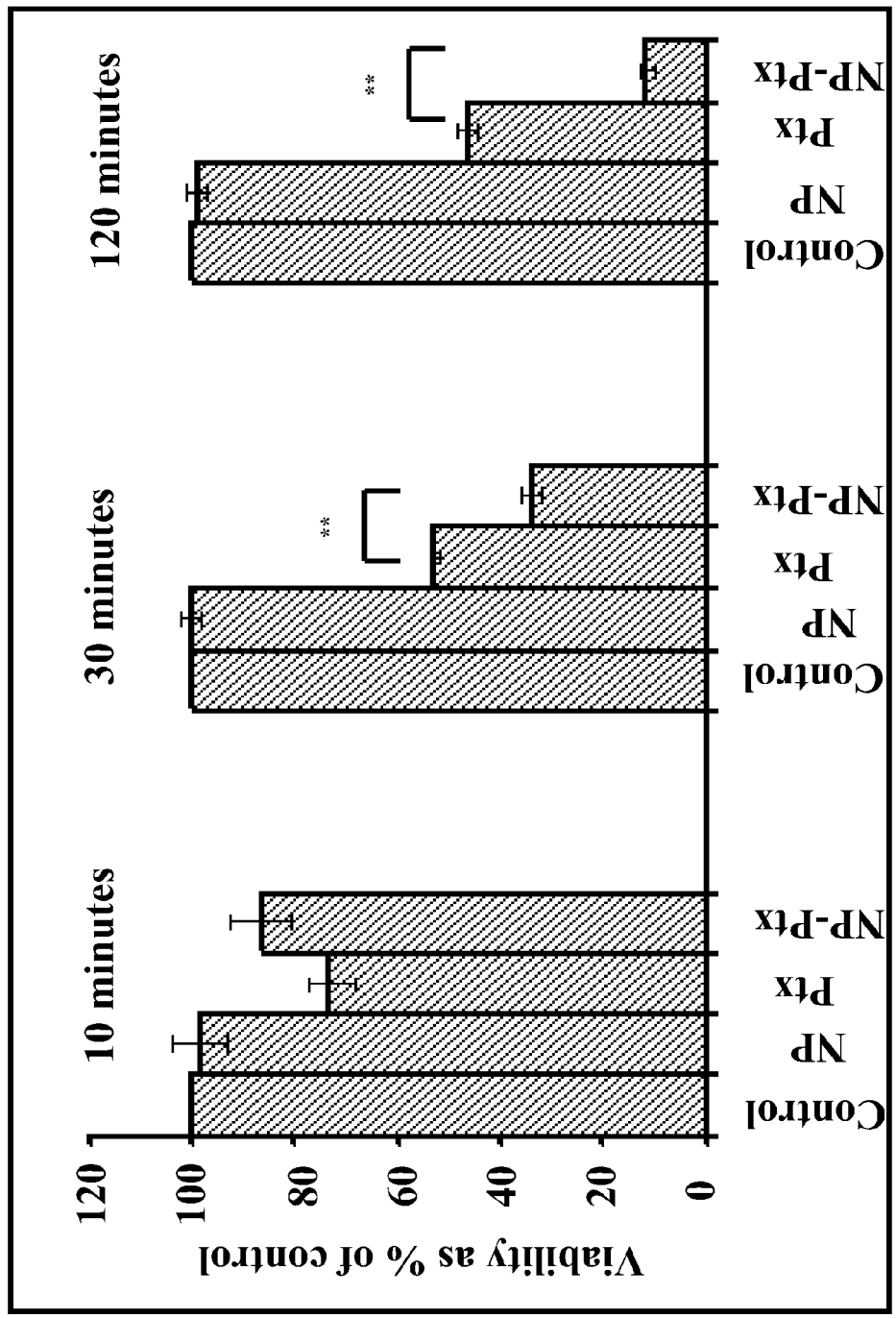

In vitro Anti-Tumoral Activity of Ptx-Loaded GGbPEG Nanoparticles:

MTT assay was used to evaluate the cytotoxicity of Ptx-loaded GGbPEG nanoparticles. Human prostate cancer cells, DU-145 (FIG. 16A) or PC-3 (FIG. 16B) treated with 25 µg/ml of either Ptx in solution or encapsulated formulations for various time points (10 minutes, 30 minutes, or 120 minutes) and incubated 72 h showed a time-dependent cytotoxicity in both cells lines. However, the results (FIGS. 16A and 16B) showed greater cytotoxicity with longer incubation period in cells treated with the encapsulated paclitaxel than the solution drug. For example, DU-145 cells (FIG. 16A) treated for 30 minutes with the solution drug and the encapsulated formulation showed 50% and 30% cell viability respectively, however increasing the treatment time to 120 min significantly ($P<0.05$) decreased the cell viability to 35% and 10% respectively after 72 h. Similar observations were made in PC-3 cells (FIG. 16B) treated with the solution drug or encapsulated formulation. Cells treated with GGbPEG nanoparticles alone did not elicit cytotoxic effect in both cell lines.

Figure 17A:
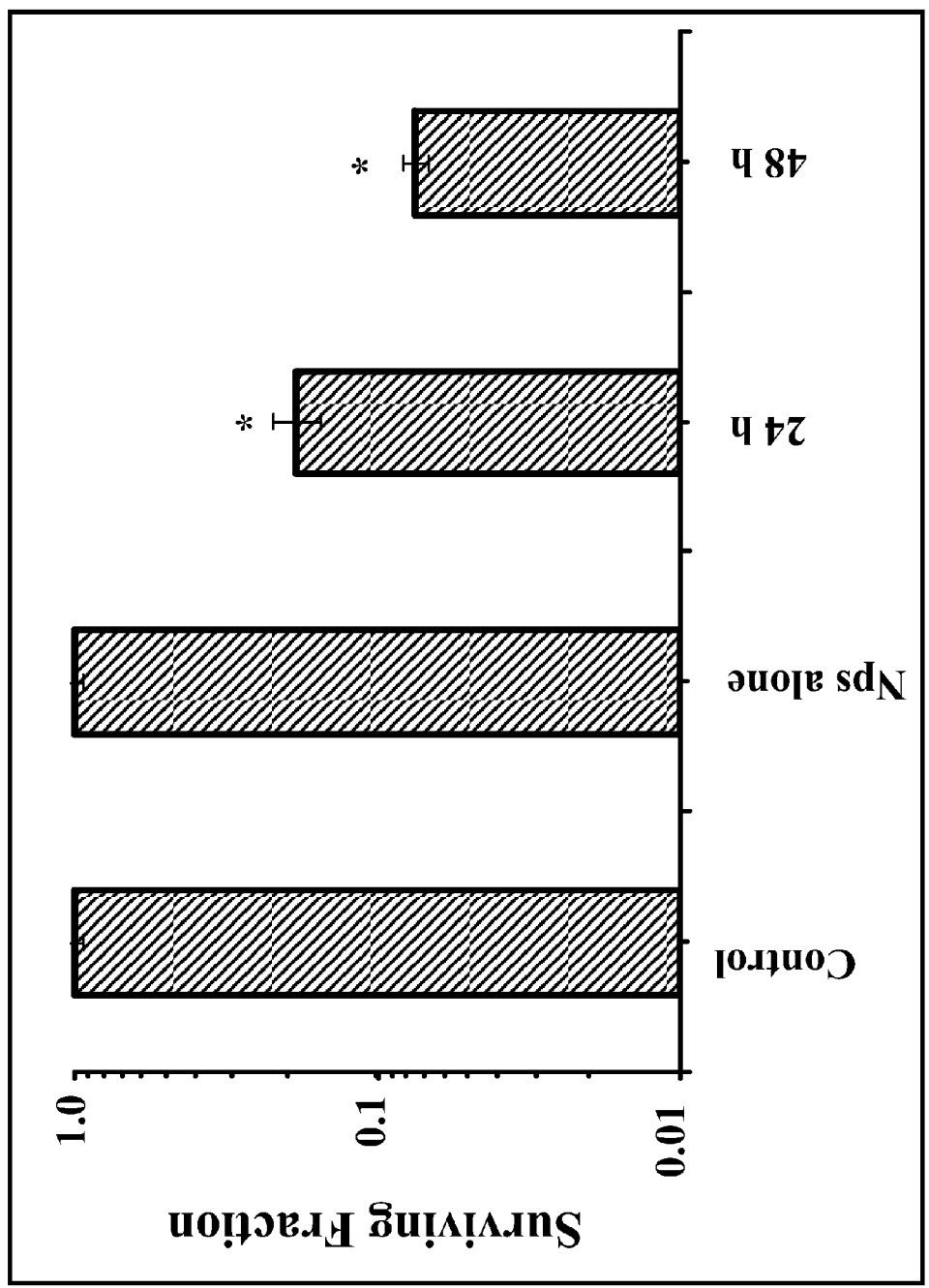
FIGS. 17A-17B graphically depict the effect of paclitaxel-loaded nanoparticles on the clonogenic survival of human prostate cancer cells DU-145 and PC-3 respectively.
Figure 17B:
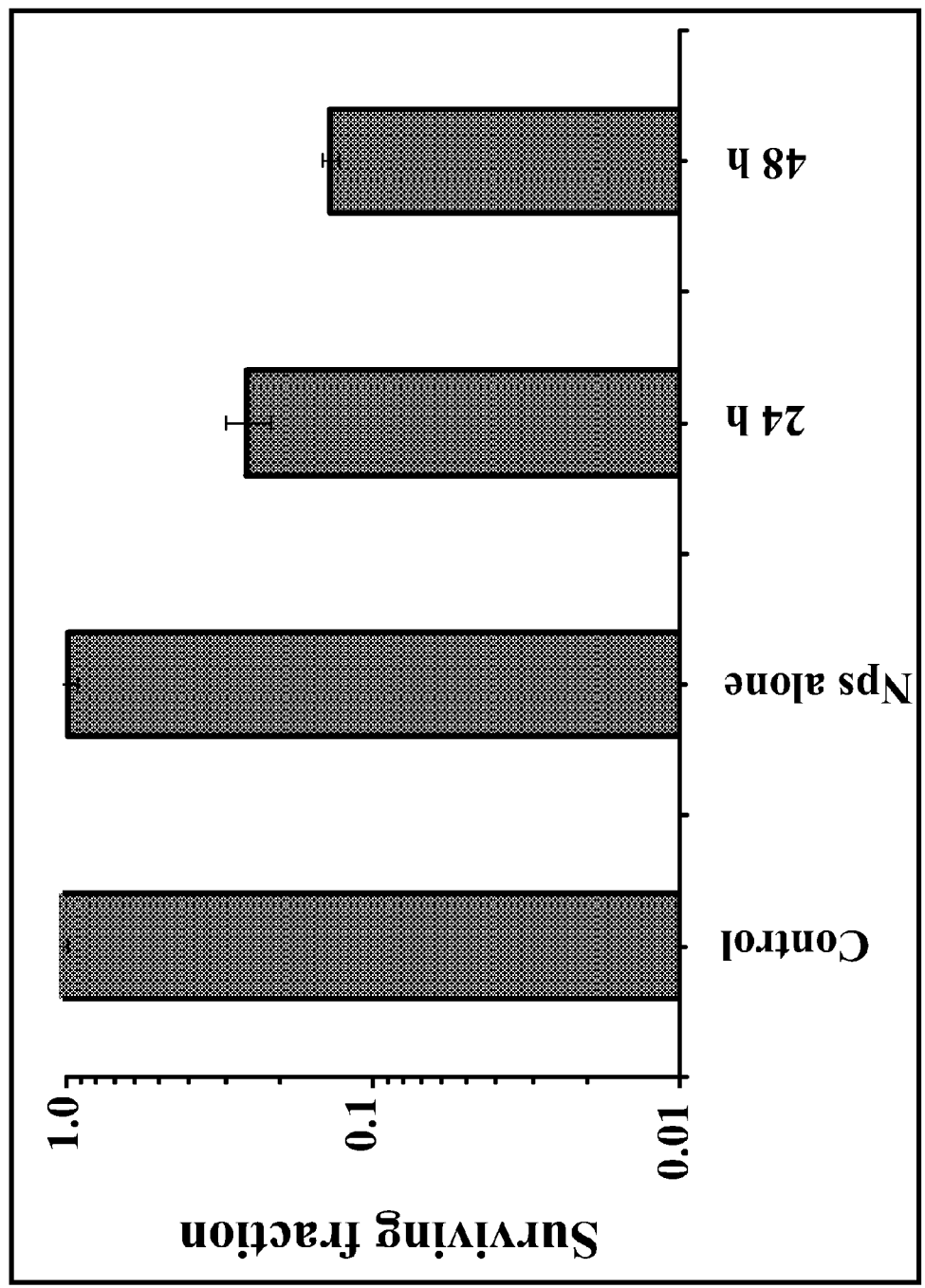

Effect of Ptx-GGbPEG Nanoparticles on the Clonogenic Survival of Human Prostate Carcinoma Cells To determine the long-term effect of Ptx-GGbPEG nanoparticles on human prostate cancer cells, clonogenic survival analysis was performed. Significant (p<0.05) decrease in surviving fractions with increased incubation time was observed (FIGS. 17A-17B). For example, DU-145 clones (FIG. 17A) treated for 24 h or 48 h showed surviving fractions of 0.19±0.062 and 0.075±0.03 respectively, as compared to the untreated controls with a surviving fraction of 1.0. Similarly, PC-3 cells (FIG. 17B) treated with paclitaxel-loaded nanoparticles for 24 h or 48 h showed surviving fractions of 0.26±0.01 and 0.14±0.02 respectively. Furthermore, the data showed decreases in both the number and size of colonies in both cell lines exposed to Ptx-GGbPEG nanoparticles.

In vivo Studies Using Athymic Nude Mice Bearing Human Xenograft Prostate Cancer Tumor:

To evaluate the in vivo efficacy of Ptx-GGbPEG-Apt copolymeric nanoparticles, PC-3 cells were injected subcutaneously in the flanks of athymic nude mice as described above. When palpable tumors (~150 mm$^3$) were obtained, comparative efficacy studies were performed by dividing animals into five groups (n=4) in a way to minimize weight and tumor size differences among the groups and the following regimens were administered by a single injection via the tail vein: (i) saline; (ii) GGbPEG nanoparticles without drug; (iii) Ptx solution, 40 mg/kg; (iv) Ptx-GGbPEG nanoparticles, 40 mg/kg; or (v) Ptx-GGbPEG-Apt, 40 mg/kg. The tumor size and body weight were then monitored for 60 days.

Figure 18:
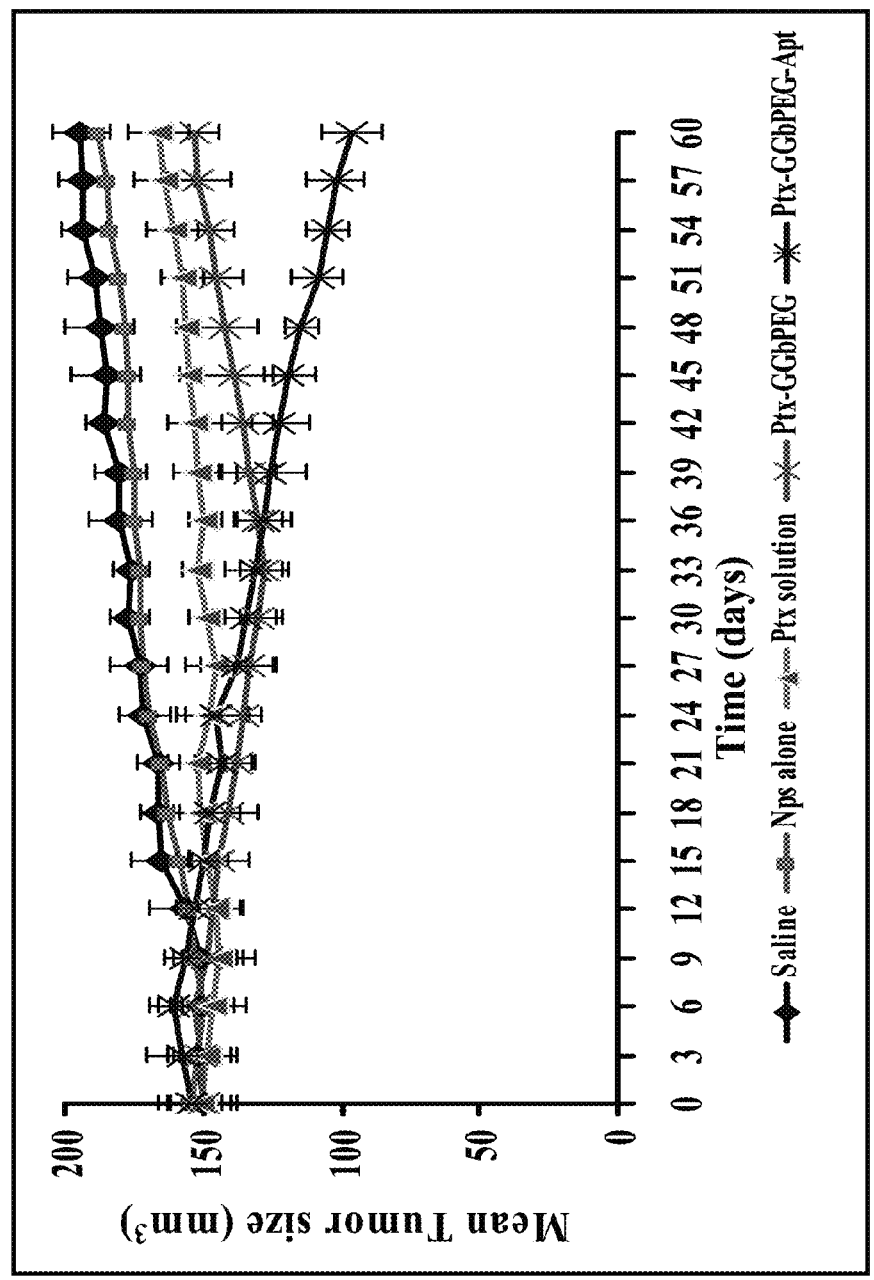
FIG. 18 depicts treatment of PC-3 tumors with saline, GGbPEG, Ptx, Ptx-GGbPEG, and Ptx-GGbPEG-Apt.

The results (FIG. 18) showed that a single intravenous administration of Ptx-GGbPEG-Apt bioconjugates was significantly more efficacious in tumor reduction as compared with nontargeted nanoparticles and controls. One reason for this enhanced efficacy may be that the targeted particles were designed to bind to the PSMA proteins on prostate cancer cells, thus possibly delaying clearance from the site of the tumor. For each control group of saline, GGbPEG, and Ptx, the treatment does not show any significant long-term efficacy, and the mean tumor sizes at the end of the study for the groups were 194.1 mm$^3$, 187.9 mm$^3$, and 166.2 mm$^3$, respectively. None of the animals of the saline and GGbPEG groups exhibited tumor regression. The difference in the final mean tumor size or survival time for the Ptx-treated group compared with the saline and GGbPEG groups was not statistically significant. The Ptx-GGbPEG-Apt-treated group demonstrated the most efficacy with a final mean tumor volume of 96.2 mm$^3$, significantly (p<0.05) smaller than all the other groups. All mice in the Ptx-GGbPEG-Apt group survived the 60 day study duration. In addition, the Ptx-GGbPEG group was more efficacious than the Ptx, GGbPEG and saline control groups, but significantly less efficacious when compared with the Ptx-GGbPEG-Apt group as shown in FIG. 18.

Figure 19:
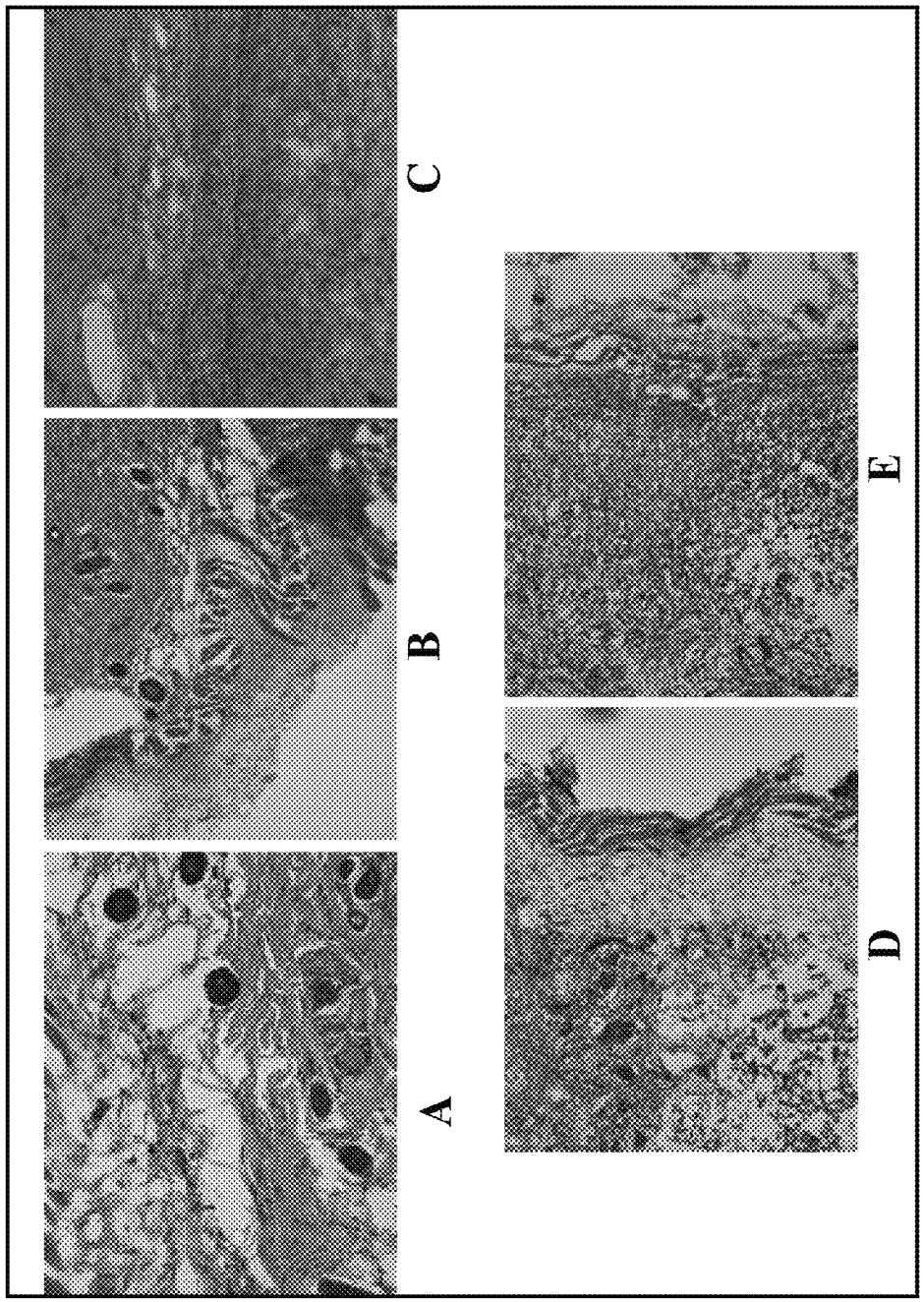
FIG. 19 graphically depicts the histological analysis of excised PC-3 tumors treated with (a) saline, (b) GGbPEG, (c) Ptx, (d) Ptx-GGbPEG, and (e) Ptx-GGbPEG-Apt.

Histological Analysis of Tumor:

Histological staining of the excised tumors was performed and the slides were evaluated by an independent pathologist. Histological examination of tumors by H & E staining at day 60 post treatment showed that saline and GGbPEG treated tumor cells had well-defined cell borders and hyperchromatic nuclei (FIG. 19, designated "A" and "B" respectively). In addition, the cytoplasm of these cells was vesicular and eosinophilic, with evidence of mitoses. On the other hand, tumors treated with Ptx (FIG. 19, designated "C"), Ptx-GGbPEG (FIG. 19, designated "D"), or Ptx-GGbPEG-Apt (FIG. 19, designated "E"), were extensively necrotic, characterized by loss of nuclear staining and cellular details. These data suggested that in the treated groups, the remaining tumor mass at day 60 post treatment consisted largely of dead or dying tumor cells.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A composition comprising a reaction product of gellan gum covalently bonded to polyethylene glycol, wherein the reaction product comprises gellan gum-b-PEG-COOH with an amide bond linkage between the gellan gum and polyethylene glycol.

2. The composition of claim 1, wherein the reaction product comprises nanoparticles of gellan gum covalently bonded to polyethylene glycol.

3. The composition of claim 2, wherein the nanoparticles have an average particle size ranging from about 50 nm to about 1000 nm.

4. The composition of claim 2, further comprising a biologically active substance complexed with the nanoparticles.

5. The composition of claim 4, wherein the biologically active substance comprises an anti-carcinogenic compound, a protein or a small molecule.

6. The composition of claim 2, further comprising a bifunctional ligand covalently bonded to the nanoparticles, said bifunctional ligand comprising (i) a first functional group capable of covalently bonding to a moiety on the nanoparticle and (ii) another moiety thereon that provides an affinity for a material.

7. The composition of claim 6, further comprising a biologically active substance complexed with the nanoparticles.

8. A method of delivering a drug to a patient, said method comprising:

administering an effective amount of a drug delivery complex to the patient, the drug delivery complex comprising (i) a reaction product of gellan gum covalently bonded to polyethylene glycol, and (ii) a biologically active substance, wherein (i) the reaction product comprises nanoparticles comprising gellan gum-b-PEG-COOH with an amide bond linkage between the gellan gum and polyethylene glycol, and the biologically active substance comprises an anti-carcinogenic compound, a protein or a small molecule.

9. The composition of claim 5, wherein the biologically active substance comprises an anti-carcinogenic compound.

10. A composition comprising (i) nanoparticles comprising a reaction product of gellan gum covalently bonded to polyethylene glycol, wherein the nanoparticles further comprise surface functionality in the form of bifunctional ligands covalently bonded thereto, and (ii) a biologically active substance complexed with the nanoparticles.

11. The composition of claim 10, wherein said bifunctional ligands comprise (i) a first functional group capable of covalently bonding to a moiety on the nanoparticle and (ii) another moiety thereon that provides an affinity for a material within a patient.

12. The composition of claim 11, wherein said material comprises a protein.

13. The composition of claim 11, wherein said bifunctional ligands comprise RNA aptamer ligands.

* * * * *

```
                            SEQUENCE LISTING

<160> NUMBER OF SEQ ID NOS: 1

<210> SEQ ID NO 1
<211> LENGTH: 56
<212> TYPE: RNA
<213> ORGANISM: Artificial Sequence
<220> FEATURE:
<223> OTHER INFORMATION: RNA-aptamer custom synthesized by RNA-TEC
      (Leuven, Belgium)

<400> SEQUENCE: 1
gggaggacga ugcggaucag ccauguuuac gucacuccuu gucaauccuc aucggc         56
```